US008765408B2

(12) United States Patent
Blattner et al.

(10) Patent No.: US 8,765,408 B2
(45) Date of Patent: Jul. 1, 2014

(54) PROPHAGE ELEMENT-FREE BACTERIA

(75) Inventors: Frederick R. Blattner, Madison, WI (US); John W. Campbell, Oak Park, IL (US); David Frisch, Fitchburg, WI (US); Guy Plunkett, III, Madison, WI (US); Gyorgy Posfai, Szeged (HU)

(73) Assignee: Wisconsin Alumni Research Foundation, Madison, WI (US)

( * ) Notice: Subject to any disclaimer, the term of this patent is extended or adjusted under 35 U.S.C. 154(b) by 123 days.

(21) Appl. No.: 13/363,848

(22) Filed: Feb. 1, 2012

(65) Prior Publication Data

US 2012/0219994 A1    Aug. 30, 2012

Related U.S. Application Data

(63) Continuation-in-part of application No. 11/400,711, filed on Apr. 7, 2006, now Pat. No. 8,119,365, which is a continuation-in-part of application No. 11/275,094, filed on Dec. 9, 2005, now Pat. No. 8,039,243, which is a continuation-in-part of application No. 10/896,739, filed on Jul. 22, 2004, now abandoned, which is a continuation of application No. PCT/US03/01800, filed on Jan. 22, 2003, which is a continuation-in-part of application No. 10/057,582, filed on Jan. 23, 2002, now Pat. No. 6,989,265.

(60) Provisional application No. 60/634,611, filed on Dec. 9, 2004, provisional application No. 60/409,089, filed on Sep. 6, 2002.

(51) Int. Cl.
   *C12P 21/06* (2006.01)
   *C12N 1/20* (2006.01)
   *C12N 1/21* (2006.01)

(52) U.S. Cl.
   USPC .................. 435/69.1; 435/252.33; 435/252.8

(58) Field of Classification Search
   None
   See application file for complete search history.

(56) References Cited

U.S. PATENT DOCUMENTS

| | | | | |
|---|---|---|---|---|
| 4,851,348 | A | 7/1989 | Hanahan | 435/6 |
| 4,981,797 | A | 1/1991 | Jessee et al. | 435/252.8 |
| 5,578,464 | A | 11/1996 | Lunn et al. | 435/69.1 |
| 5,747,662 | A | 5/1998 | Simmons et al. | 536/24.1 |
| 5,824,502 | A | 10/1998 | Honjo et al. | 435/69.1 |
| 5,962,327 | A | 10/1999 | Dujon et al. | 435/478 |
| 6,015,709 | A | 1/2000 | Natesan | 435/366 |
| 6,022,952 | A | 2/2000 | Weiner et al. | 530/350 |
| 6,117,680 | A | 9/2000 | Natesan et al. | 435/455 |
| 6,238,924 | B1 | 5/2001 | Dujon et al. | 435/477 |
| 6,335,178 | B1 | 1/2002 | Weiner et al. | 435/69.1 |
| 6,372,476 | B1 | 4/2002 | Belguith et al. | 435/233 |
| 6,410,273 | B1 | 6/2002 | Crouzet et al. | 435/91.1 |
| 6,509,156 | B1 | 1/2003 | Stewart et al. | 435/6 |
| 6,989,265 | B2 | 1/2006 | Blattner et al. | 435/252.8 |
| 8,039,243 | B2 | 10/2011 | Blattner | 435/252.8 |
| 8,119,365 | B2 | 2/2012 | Blattner et al. | 435/69.1 |
| 2003/0138937 | A1 | 7/2003 | Blattner et al. | 435/252.33 |
| 2005/0032225 | A1 | 2/2005 | Blattner et al. | 435/488 |

FOREIGN PATENT DOCUMENTS

| | | |
|---|---|---|
| EP | 0177343 | 4/1986 |
| EP | 0283726 | 9/1988 |
| WO | WO 88/05821 | 8/1988 |
| WO | WO 96/14408 | 5/1996 |
| WO | WO 01/27258 | 4/2001 |
| WO | WO 02/14495 | 2/2002 |
| WO | WO 03/048374 | 6/2003 |
| WO | WO 03/070880 | 8/2003 |
| WO | WO 2005/087940 | 9/2005 |
| WO | WO 2007/118162 | 10/2007 |

OTHER PUBLICATIONS

Aristidou et al., "Modification of central metabolic pathway in *Escherichia coli* to reduce acetate accumulation by heterologous expression of the bacillus subtilis acetolactate synthase gene," *Biotechnology and Bioengineering*, 44:944-951, 1994.
Asai et al., "An *Escherichia coli* strain with all chromosomal rRNA operons inactivated: complete exchange of rRNA genes between bacteria," *Proc. Natl. Acad. Sci., USA*, 96:1971-1976, 1999.
Balbas, "Understanding the art of producing protein and non-protein molecules in *E. coli*," *Molec Biotechnol.*, 19:251-267, 2001.
Baneyx, "Recombinant protein expression in *E. coli*," *Curr Opin Biotech*, 10:411-421, 1999.
Bass et al., "Mulitcopy suppressors of Prc mutant *Escherichia coli* include two HtrA (DegP) protease homologs (HhoAB), DksA, and a truncated R1pA," *Journal of Bacteriology*, 178(4):1154-1161, 1996.
Beaulieu et al., "Pathogenic behavior of pectinase-defective *Erwinia chrysanthemi* mutants on different plants," *MPMI*, 6(2):197-202, 1993.
Bermejo et al., "Expression of clostridium acetobutylicum ATCC 824 genes in *Escherichia coli* for acetone production and acetate detoxification," *Applied and Environmental Microbiology*, 64:1079-1085, 1998.
Berry et al., "Application of metabolic engineering to improve both production and use of biotech indigo," *J Indust Micro & Biotech*, 22:127-133, 2002.

(Continued)

*Primary Examiner* — Nancy T Vogel
(74) *Attorney, Agent, or Firm* — Parker Highlander PLLC

(57) ABSTRACT

The present invention provides a bacterium having a genome that is genetically engineered to be smaller than the genome of its native parent strain. A bacterium with a smaller genome can produce a commercial product more efficiently. The present invention also provides methods for deleting genes and other DNA sequences from a bacterial genome. The methods provide precise deletions and seldom introduces mutations to the genomic DNA sequences around the deletion sites. Thus, the methods can be used to generate a series of deletions in a bacterium without increasing the possibility of undesired homologous recombination within the genome. In addition, some of the methods provided by the present invention can also be used for replacing a region of a bacterial genome with a desired DNA sequence.

11 Claims, 10 Drawing Sheets

(56) References Cited

OTHER PUBLICATIONS

Blattner et al., "The complete genome sequence of *Escherichia coli* K-12," *Science*, 277:1453-1474, 1997.

Blaudeck et al., "Specificity of single peptide recognition in TAT-dependent bacterial protein translocation," *J. Bacteriology*, 183:604-610, 2001.

Chang et al., "Acetate metabolism in a pta mutant of *Escherichia coli* W3110: Importance of maintaining acetyl coenzyme a flux for growth and survival," *Journal of Bacteriology*, 181:6656-6663, 1999.

Chou et al., "Effect of modified glucose uptake using genetic engineering techniques on high-level recombinant protein production in *Escherichia coli* dense cultures," *Biotechnology and Bioengineering* 44:953-960, 1994.

Contiero et al., "Effects of mutations in acetate metabolism on high-cell-density growth of *Eschrichia coli*," *Journal of Industrial Microbiology & Biotechnology*, 24:421-430, 2000.

Court et al., "Genetic engineering using homologous recombination," *Annu Rev Genet*, 36:361-388, 2002.

Danese et al., "Targeting and assembly of periplasmic and outer-membrane proteins in *Escherichia coli*," *Annu Rev Genet*, 32:59-64, 1998.

Database EMBL, "*E.coli* genomic DNA, Kohara clone #421(55.1-55.5 min.)," Database Acession No. ECD874.

Datsenko and Wanner, "One-step inactivation of chromosomal genes in *Escherichia coli* K-12 using PCR products," *Proc. Natl. Acad. Sci. USA*, 97:6640-6645, 2000.

Dedhia et al., "Overproduction of glycogen in *Escherichia coli* blocked in the acetate pathway improved cell growth," *Biotechnology and Bioengineering*, 44:132-139, 1994.

Degryse, "Evaluation of *Escherichia coli* recBC sbcBC mutants for cloning by recombination in vivo," *J. Biotechnology*, 39:181-187, 1995.

DeLisa et al., "Quorum sensing via AI-2 communicates the metabolic burden associated with heterologous protein production in *E. coli*," *Biotech Bioeng*, 75(4):439-450, 2001.

Diaz-Ricci et al., "Effects of alteration of the acetic acid synthesis pathway on the fermentation pattern of *Escherichia coli*," *Biotechnology and Bioengineering*, 38:1318-1324, 1991.

Dykstra and Kushner, "Physical characterization of the cloned protease III gene from *Escherichia coli* K-12," *Journal of Bacteriology*, 163(3):1055-1059, 1985.

Eichhorn et al., "Deletion analysis of the *Escherichia coli* taurine and alkanesulfonate transport systems," *Journal of Bacteriology*, 182(10)2687-2695, 2000.

Farmer and Liao., "Reduction of aerobic acetate production by *Escherichia coli*," *Applied and Environmental Microbiology*, 63:3205-3210, 1997.

Fekkes and Driessen, "Protein targeting to the bacterial cytoplasmic membrane," *Microbiol. Mol. Biol. Rev.*, 63:161-193, 1999.

GenBank Accession No. AE014073, 2006.
GenBank Accession No. AE014075, 2006.
GenBank Accession No. AF348706, 2007.
GenBank Accession No. AP009048, 2008.
GenBank Accession No. U00096, 2006.

Gill et al., "A comparative study of global stress gene regulation in response to overexpression of recombinant proteins in *E. coli*," *Metabolic Engineering*, 2:178-189, 2000.

Hahm et al., "Characterization and evaluation of a pta (phoshotransacetylase) negative mutant of *Escherichia coli* HB101 as production host of foreign lipase," *Applied Microbiology and Biotechnology*, 42:100-107, 1994.

Hall, "Activation of the bgl operon by adaptive mutation," *Mol. Biol. Evol.*, 15:1-5, 1998.

Hanahan, "Studies on transformation of *Escherichia coli* with plasmids," *J. Mol. Biol.*, 166(4):557-580, 1983.

Hannig and Makrides, "Strategies for optimizing heterologous protein expression in *Escherichia coli*," *Trends Biotechnol.*, 16(2):54-60, 1998.

Hayashi et al., "Construction of a genetic linkage map of the model legume *Lotus japonicus* using an intraspecific F2 population," *DNA Research*, 8:11-22, 2001.

Hengen, "Better competent cells and DNA polymerase contaminants," *Trends in Biochem. Sci.*, 19:426-427, 1994.

Hengen, "Preparing ultra-competent *Escherichia coli*," *Trends in Biochem. Sci.*, 21:75-76, 1996.

Hockney, "Recent developments in heterologous protein production in *Escherichia coli*," *Trends Biotechnol.*, 12(11):456-632, 1994.

Holms, "Flux analysis and control of the central metabolic pathways in *Escherichia coli*," *FEMS Microbiology Reviews*, 19:85-116, 1996.

Holms, "The central metabolic pathways of *Escherichia coli*: relationship between flux and control at a branch point, efficiency of conversion to biomass, and excretion of acetate," *Current Topics in Cellular Regulation*, 28:69-105, 1986.

Hynds et al., "The sec-independent twin-arginine translocation system can transport both tightly folded and malfolded proteins across the thylakoid membrane," *J. Biol. Chem.*, 273:34868-34874, 1998.

Kakuda et al., "Construction of Pta-Ack pathway deletion mutants of *Escherichia coli* and characteristic growth profiles of the mutants in a rich medium," *Bioscience Biotechnology Biochemistry*, 58:2232-2235, 1994.

Khosla et al., "Expression of Recombinant Proteins in *Escherichia coli* Using an Oxygen-Responsive Promoter," *Bio/Technology*, 8:554-558, 1990.

Kitamura et al., "DNA sequence changes in mutations in the ton B gene on the chromosome of *Escherichia coli* K-12: insertion elements dominate the spontaneous spectra,," *Jpn J. Genet*, 70:35-46, 1995.

Kolisnychenko et al., "Engineering a reduced *Escherichia coli* genome," *Genome Research*, 12:640-647, 2002.

Koob et al., "Minimizing the genome of *Escherichia coli*," *Ann NY Acad Science*, 745:1-3, 1994.

Koonin, "How many genes can make a cell: the minimal-gene-set concept," *Ann Rev Genome Hum Genet*, 1:99-116, 2000.

Lee, "High cell-density culture of *Escherichia coli*," *TIBTECH*, 14:98-103, 1996.

Mersereau et al., "Efficient transformation of *Agrobacterium tumefaciens* by electroporation," *Gene*, 90:149-151, 1990.

Murphy, "Use of bacteriophage λ recombination functions to promote gene replacement in *Escherichia coli*," *J. Bacteriol.*, 180:2063-2071, 1998.

Muyrers et al., "Rapid modification of bacterial artificial chromosomes by ET-recombination," *Nucleic Acids Research*, 27:1555-1557, 1999.

Neidhardt et al., "Culture medium for Enterobacteria," *J. Bacteriol.*, 119:736-747, 1974.

Office Communication issued in European patent application No. 07760207.6, dated Jul. 31, 2009.

Office Communication issued in U.S. Appl. No. 11/400,711, dated Mar. 6, 2009.

Office Communication issued in U.S. Appl. No. 11/400,711, dated Dec. 1, 2010.

Office Communication issued in U.S. Appl. No. 11/400,711, dated Jul. 22, 2009.

Office Communication issued in U.S. Appl. No. 11/400,711, dated Apr. 8, 2011.

Office Communication issued in U.S. Appl. No. 11/400,711, dated Aug. 9, 2011.

Oliner et al., "In vivo cloning of PCR products in *E. coli*," *Nucleic Acids Research*, 2(22):5192-5197, 1993.

Otto and Silhavy, "Surface sensing and adhesion of *E. coli* controlled by the Cpx-signaling pathway," *Proc. Natl. Acad. Sci., USA*, 99(4):2287-2292, 2002.

Park et al., "MppA, a periplasmic binding protein essential for import of the bacterial cell wall peptide L-Ananyl-γ-D-glutamyl-meso-diaminopimelate," *Journal of Bacteriology*, 180(5):1215-1223, 1998.

Passoth et al., "Analysis of the hypoxia-induced ADH2 promoter of the respiratory yeast *Pichia stipitis* reveals a new mechanism for sensing of oxygen limitation in yeast," *Yeast*, 20:39-51, 2003.

PCT/US2007/066087 International Search Report, mailed Sep. 17, 2007.

(56) References Cited

OTHER PUBLICATIONS

Perna et al., "Genome sequence of enterohemorrhagic *Escherichia coli* O157:H7," *Nature*, 409:529-533, 2001.
Perna et al., "The genomes of *Escherichia coli* K-12 and pathogenic *E. coli*," *Pathogenic E. coli Paradigm for Bacterial Pathogenesis*, M.S. Donnenberg, Editor, Academmic Press, 2002.
Pfeifer et al., "Biosynthesis of complex polyketides in metabolically engineered strain of *E. coli*," *Science* 291:1790-1792, 2001.
Ponce, "Effect of growth rate reduction and genetic modifications of acetate accumulation and biomass yields in *Escherichia coli*," *Biotechnology and Bioengineering*, 87:775-780, 1999.
Pope and Kent, "High efficiency 5 min transformation of *Escherichia coli*," *Nucleic Acids Research*, 24:536-537, 1996.
Posfai et al., "Emergent properties of reduced-genome *Escherichia coli*," *Science*, 312:1044-1046, 2002.
Posfai et al., "In vivo excision and amplification of large segments of the *Escherichia coli* genome," *Nucleic Acids Research*, 22(12):2392-2398, 1994.
Posfai et al., "Markerless gene replacement in *Escherichia coli* stimulated by a double-strand break in the chromosome," *Nucleic Acids Research*, 27:4409-4415, 1999.
Posfai et al., "Versatile insertion plasmids for targeted genome manipulations in bacteria: isolation, deletion, and rescue of the pathogenicity island LEE of the *Escherichia coli* O157:H7 genome," *J. Bacteriol.*, 179:4426-4428, 1997.
Pugsley, "The complete general secretory pathway in gram-negative bacteria," *Microbiol. Rev.*, 57:50-108, 1993.
Riesenberg, "High cell density cultivation of *E. coli* at controlled specific growth rate," *J. Biotech*, 20(10):17-27, 1991.
Riggs, "Expression and Purification of Maltose-Binding Protein Fusions," *Current Protocols Mol. Biol.*, 16.6.1-16.6.14, John Wiley and Sons, 1994.
Ritz and Beckwith, "Roles of thiol redox pathways in bacteria," *Annu Rev Microbiol*, 55:21-48, 2001.
Santini et al., "A novel sec-independent periplasmic protein translocation pathway in *Escherichia coli*," *EMBO J.*, 17:101-112, 1998.
Sargent et al., "Overlapping functions of components of a bacterial sec-independent protein export pathway," *EMBO J*, 17:3640-3650, 1998.
Schaechter and Neidhardt, "Introduction," In: *Escherichia coli and Salmonella*, ed. Neidhart, FC et al., 1-2, ASM Press, Washington, D.C., 1997.
Schutz et al., "Sulfide-quinone reductase from Rhodobacter capsulatus: requirement for growth, periplasmic localization, and extension of gene sequence analysis," *Journal of Bacteriology*, 181(20):6516-6523, 1999.
Selinger et al., "RNA expression analysis using a 30 base pair resolution *Escherichia coli* genome array," *Nat Biotechnol*, 18(12):1262-1268, 2000.
Sharma et al., "Recombinant protein production in an *Escherichia coli* reduced genome strain," *Metabolic Engineering*, 9:133-141, 2007.
Shiloach and Fass, "Growing *E. coli* to high cell density—A historical perspective on method development," *Biotechnology Advances*, 23:345-357, 2005.
Shiloach et al. "Effect of glucose supply strategy on acetate accumulation, by *Escherichia coli* BL21 (lambda-DE3)and *Escherichia coli* JM109," *Biotechnology and Bioengineering*, 49:421428, 1996.
Shuman, "Active transport of maltose in *Escherichia coli* K12," *J. Biol. Chem.*, 257(10):5455-5461, 1982.
Simmons and Yansura, "Translational level is a critical factor for secretion of heterologous proteins in *E. coli*," *Nature*, 14:629-634, 1996.
Singh-Gasson et al., "Maskless fabrication of light-directed oligonucleotide microarrays using a digital micromirror array," *Nat Biotechnol.*, 17(10):974-978, 1999.
Smalley et al., "In search of the minimal *Escherichia coli* genome," *Trends in Microbiology*, 11(1):6-8, 2003.
Swartz, "Advances in *E. coli* production of therapeutic proteins," *Curr. Opin in Biotech*, 12:195-201, 2001.
Thomas et al., "Export of active green fluorescent protein to the periplasm by the twin-arginine translocase (TAT) pathway in *Escherichia coli*," *Mol Micro*, 39(1):47-53, 2001.
Van Spanning et al., "Isolation and characterization of the moxJ, moxG, moxI, and moxR genes of *Paracoccus denitrificans*: Inactivation of moxJ, moxG, and moxR and the resultant effect on methylotrophic growth," *Journal of Bacteriology*, 173(21):6948-6961, 1991.
Vellai et al., "Genome economization and a new approach to the species concept in bacteria," *Proc R Soc Lond B*, 266:1953-1958, 1999.
Venkatesan et al., "Complete DNA sequence and analysis of the large virulence plasmid of Shigella flexneir.," *Infection of Immunity*, 3271-3285, 2001.
Waller and Sauer, "Characterization of degQ and degS, *Escherichia coli* genes encoding homologs of the DegP protease," *Journal of Bacteriology*, 178(4):1146-1153, 1996.
Weiner et al., "A novel and ubiquitous system for membrane targeting and secretion of cofactor-containing proteins," *Cell*, 93:93-101, 1998.
Welch et al., "Extensive mosaic structure revealed by the complete genome sequence of uropathogenic *Escherichia coli*," *Proc. Natl. Acad. Sci., USA*, 99(26):17020-17024, 2002.
Wirth et al., "Transformation of various species of gram-negative bacteria belonging to 11 different genera by electroporation," *Mol. Gen. Genet.*, 216:175-177, 1989.
Xu and Tabita, "Positive and negative regulation of sequences upstream of the form II cbb CO2 fixation operon of *Rhodobacter sphaeroides*," *J. Bacteriol.*, 176:7299-7308, 1994.
Yang et al., "Metabolic flux analysis of *Escherichia coli* deficient in the acetate production pathway and expressing the bacillus subtilis acetolactate synthase," *Metabolic Engineering* 1:26-34, 1999.
Yu et al., "An efficient recombination system for chromosome engineering in *Escherichia coli*," *Proc. Natl. Acad. Sci., USA*, 97:5978-5983, 2000.
Yu et al., "Minimization of the *Escherichia coli* genome using a Tn5-targeted Cre/LoxP excision system," *Nature Biotech*, 20:1018-1023, 2002.f.
Zhang et al., "A new logic for DNA engineering using recombination in *Escherichia coli*," *Nature Genetics*, 20:123-128, 1998.
Zhang et al., "DNA cloning by homologous recombination in *Escherichia coli*," *Nature Biotech.*, 18:1314-1317, 2000.
Zhang et al., "Phage annealing proteins promote oligonucleotide-directed mutagenesis in *Escherichia coli* and mouse ES cells," *BMC Molecular Biology*, 4:1, 2003.

Growth of MG1655 and MDS62 following the addition of bicyclomycin

PROPHAGE ELEMENT-FREE BACTERIA

CROSS-REFERENCE TO RELATED APPLICATIONS

This application is a continuation-in-part of U.S. application Ser. No. 11/400,711, filed Apr. 7, 2006, which is a continuation-in-part of U.S. application Ser. No. 11/275,094, filed Dec. 9, 2005, which claims the benefit of U.S. Provisional Application No. 60/634,611, filed Dec. 9, 2004 and which is a continuation-in-part of U.S. application Ser. No. 10/896,739, filed Jul. 22, 2004 (abandoned), which is a continuation of International Application No. PCT/US03/01800, filed Jan. 22, 2003, which claims the benefit of U.S. Provisional Application No. 60/409,089, filed Sep. 6, 2002 and which is a continuation-in-part of U.S. application Ser. No. 10/057,582, filed Jan. 23, 2002 (now U.S. Pat. No. 6,989,265), each of which is incorporated herein by reference.

STATEMENT REGARDING FEDERALLY SPONSORED RESEARCH OR DEVELOPMENT

This invention was made with government support under GM35682 awarded by the National Institutes of Health. The government has certain rights in the invention.

BACKGROUND OF THE INVENTION

Bacteria have been used to produce a wide range of commercial products. For example, many *Streptomyces* strains and *Bacillus* strains have been used to produce antibiotics; *Pseudomonas denitrificans* and many *Propionibacterium* strains have been used to produce vitamin B12; some other bacteria have been used to produce vitamin Riboflavin; *Brevibacterium flavum* and *Corynebacterium glutamicum* have been used to produce lysine and glutamic acid, respectively, as food additives; other bacteria have been used to produce other amino acids used as food additives; *Alcaligenes eutrophas* has been used to produce biodegradable microbial plastics; and many *Acetobacter* and *Gluconobacter* strains have been used to produce vinegar. More recently, it has become common for bacteria, such as *Escherichia coli* (*E. coli*), to be genetically engineered and used as host cells for the production of biological reagents, such as proteins and nucleic acids, in laboratory as well as industrial settings. The pharmaceutical industry supports several examples of successful products which are human proteins which are manufactured in *E. coli* cultures cultivated in a fermenter.

It is not an uncommon occurrence for normal bacterial proteins to adversely affect the production or the purification of a desired protein product from an engineered bacteria. For example, when *E. coli* bacteria are used as host cells to generate a large quantity of a desired product encoded by a gene that is introduced into the host cells by a plasmid, certain normal *E. coli* gene products can interfere with the introduction and maintenance of plasmid DNA. More significantly, because of the economies of bacterial culture in making proteins in bacteria, often the cost of purification of a recombinant protein can be more than the cost of production, and some of the natural proteins produced by the bacterial host are sensitive purification problems. Further, many bacterial strains produce toxins that must be purified away from the target protein being produced and some strains can produce, by coincidence, native proteins that are close in size to the target protein, thereby making size separation not available for the purification process.

Also, however, the genome of a bacteria used in a fermenter to produce a recombinant protein includes many unnecessary genes. A bacteria living in a natural environment has many condition responsive genes to provide mechanisms for surviving difficult environmental conditions of temperature, stress or lack of food source. Bacteria living in a fermentation tank do not have these problems and hence do not require these condition responsive genes. The bacterial host spends metabolic energy each multiplication cycle replicating these genes. Thus the unnecessary genes and the unneeded proteins, produced by a bacterial host used for production of recombinant protein, result is a lack of efficiencies in the system that could be improved upon.

It is not terribly difficult to make deletions in the genome of a microorganism. One can perform random deletion studies in organisms by simply deleting genomic regions to study what traits of the organism are lost by the deleted genes. It is more difficult, however, to make targeted deletions of specific regions of genomic DNA and more difficult still if one of the objectives of the method is to leave no inserted DNA, here termed a "scar," behind in the organism after the deletion. If regions of inserted DNA, i.e. scars, are left behind after a genomic deletion procedure, those regions can be the locations for unwanted recombination events that could excise from the genome regions that are desirable or engender genome rearrangements. In building a series of multiple deletions, scars left behind in previous steps could become artifactual targets for succeeding steps of deletion. This is especially so when the method is used repeatedly to generate a series of deletions from the genome. In other words, the organism becomes by the deletion process genetically unstable if inserted DNA is left behind.

BRIEF SUMMARY OF THE INVENTION

The present invention provides methods for reducing the genome of an organism particularly without leaving scars in the genome.

In one embodiment, the present invention provides a bacterium having a genome that is genetically engineered to be at least two percent (2%) to twenty percent (20%) smaller than the genome of its native parent strain. Particularly, the genome is at least seven percent (7%) smaller than the genome of the native parent. More particularly, the genome is eight percent (8%) to fourteen percent (14%) to twenty percent (20%) smaller than the genome of its native parent strain. When used to produce a product, a bacterium with a smaller genome can have one or more of the following advantages. One, the production process can be more efficient either in terms of resource consumption or in terms of production speed, ultimate yield percent or all three. Two, the product purification process can be simplified or purer products can be made. Three, a product that cannot be produced before due to native protein interference can be produced. Four, the yield per cell of the desired product may be increased.

The present invention is also directed to an organism, particularly a bacterium, engineered to have a "clean genome," i.e., lacking, for example, genetic material such as certain genes unnecessary for growth and metabolism of the bacteria, insertion sequences (transposable element), pseudogenes, prophage, endogenous restriction-modification genes, pathogenicity genes, toxin genes, fimbrial genes, periplasmic protein genes, invasin genes, sequences of unknown function and sequences not found in common between two strains of the same native parental species of bacterium. Other DNA sequences that are not required for cell survival and production of certain proteins in culture can be deleted. The reduced genome bacteria of the present invention may be viewed as a basic genetic framework to which may be added a myriad of genetic elements for expression of useful products as well as genetic control elements which offers an unprecedented opportunity to fine tune or optimize the expression of the desired product.

The present invention also provides materials and methods for targeted deletion of genes and other DNA sequences from a bacterial genome without leaving any residual DNA from the manipulation (scarless deletion). Since the methods of the present invention seldom introduce mutations or leave residual DNA in the genomic DNA sequences around deletion sites, the methods can be used to generate a series of deletions in a bacterium without increasing the possibility of undesired homologous recombination within the genome. Some of these methods are also useful for making similar deletions, for example, in bacteriophage, native plasmids and the like, as well as in higher organisms, such as mammals and plants.

The first deletion method is linear DNA-based. To perform the process, first, a linear DNA construct is provided in a bacterium and a region of the bacterial genome is replaced by the linear DNA construct through homologous recombination aided by a system residing in the bacterium that can increase the frequency of homologous recombination. Next, a separate gene previously introduced into the bacterium expresses a sequence-specific nuclease to cut the bacterial genome at a unique recognition site located on the linear DNA construct. Then, a DNA sequence engineered to contain DNA homologous to a target in the genomic DNA at one end of the linear DNA construct undergoes homologous recombination with a similar genomic DNA sequence located close to the other end of the linear DNA construct. The net result is a precise deletion of a region of the genome.

The second method is also linear DNA-based. Two DNA sequences, one of which is identical to a sequence that flanks one end of a bacterial genome region to be deleted and the other of which is identical to a sequence that flanks the other end of the bacterial genome region to be deleted, are engineered into a vector in which the two sequences are located next to each other. At least one sequence-specific nuclease recognition site is also engineered into the vector on one side of the two sequences. The vector is introduced into a bacterium and a linear DNA is generated inside the bacterium by expressing inside the bacterium a nuclease that recognizes the sequence-specific nuclease recognition site and cuts the vector therein. The linear DNA undergoes homologous recombination with the bacterial genome aided by a system residing in the bacterium to increase the frequency of homologous recombination. A bacterium with a targeted deletion free of residual artifactual in its genome is thus produced.

The second method described above can also be used to replace a selected region of a bacterial genome with a desired DNA sequence. In this case, a desired DNA sequence that can undergo homologous recombination with and hence replace the selected region is engineered into the vector. All other aspects are the same as for deleting a targeted region.

The third method is suicide plasmid-based. The specific plasmid used in this method contains an origin of replication controlled by a promoter and a selectable marker, such as an antibiotic resistance gene. To delete a targeted region of a bacterial genome, a DNA insert that contains two DNA sequences located right next to each other, one of which is identical to a sequence that flanks one end of a bacterial genome region to be deleted and the other of which is identical to a sequence that flanks the other end of the bacterial genome region, is inserted into the plasmid. The plasmid is then introduced into the bacteria and integrated into the bacterial genome. Next, the promoter is activated to induce replication from the ectopic origin introduced into the bacterial genome so that recombination events are selected. In many bacteria, the recombination events will result in a precise deletion of the targeted region of the bacterial genome and these bacteria can be identified. An alternative way to select for recombination events is to engineer a recognition site of a sequence-specific nuclease into the specific plasmid and cut the bacterial genome with the sequence-specific nuclease after the plasmid has integrated into the bacterial genome.

The suicide plasmid-based method described above can also be used to replace a selected region of a bacterial genome with a desired DNA sequence. In this case, a DNA insert that contains a desired DNA sequence that can undergo homologous recombination with and hence replace the selected region is inserted into the plasmid. All other aspects are the same as for deleting a targeted region.

The methods of the present invention are useful inter alia for engineering reduced genome bacteria for the production of recombinant gene products. Such engineered bacteria allow improved production of such proteins by increasing the efficiency of production and yield of the desired gene product as well as allowing more efficient purification of the product by virtue of the elimination of unnecessary bacterial gene products. A particular reduced genome bacteria of the present invention is a bacteria from which one or more native genes encoding periplasmic proteins and/or membrane proteins have been deleted.

The present invention is also directed to DNAs and vectors used for carrying out the methods of the present invention, methods for preparing the DNAs and to kits containing vials which vials contain one or more DNAs or vectors of the present invention and optionally suitable buffers, primers, endonucleases, nucleotides, and polymerases.

The present invention is also directed to live vaccines comprising a reduced genome bacterium of the present invention or comprising a reduced genome bacterium of the present invention into which is introduced DNA encoding antigenic determinants of pathogenic organisms operably associated with expression control sequences which allow the expression of said antigenic determinants. Also within the scope of the present invention is a live vaccine comprising a reduced genome bacterium of the present invention in to which has been introduced a DNA, derived from a pathogenic organism and optionally having an origin of replication, said live vaccine being capable of inducing an enhanced immune response in a hose against a pathogenic organism. The DNA may be methylated at a methylation site. The invention is also directed to a live vaccine produced from a pathogenic organism by deleting from the genome of that organism the genes responsible for pathogenicity while retaining other antigenic determinants.

Other objects, features and advantages of the invention will become apparent upon consideration of the following detailed description.

DETAILED DESCRIPTION OF THE INVENTION

Figure 1:
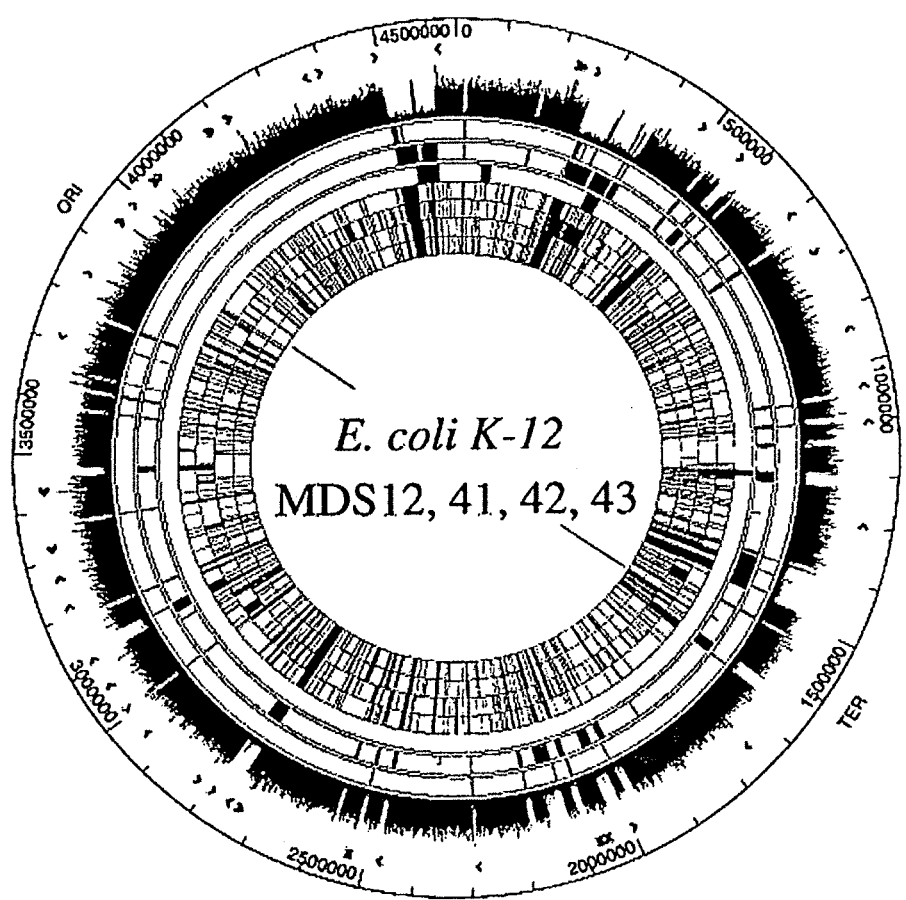
FIG. 1 shows positions of the genes and other DNA sequences on *E. coli* K-12 bacterial genome that were candidates for deletion as black and lighter hatched boxes on the outermost ring.

Bacteria in their natural environment are exposed to many conditions that are not normally experienced in standard industrial or laboratory growth, and thus carry a large number of condition-dependent, stress-induced genes or otherwise nonessential genes which may not be needed in industrial or laboratory use of the organisms. This invention began with the realization that much of the genetic information contained within the genome of a bacteria strain could be deleted without detrimental effect to use of bacteria cultures in processes of industrial or laboratory importance. It was recognized that a bacterium with a reduced genome might be advantageous over native strains in many industrial and laboratory applications. For example, a bacterium with a reduced genome is at least somewhat less metabolically demanding and thus can produce a desired product more efficiently. In addition, a reduced genome can lead to fewer native products and lower level of certain native proteins, allowing easier purification of a desired protein from the remaining bacterial proteins. Furthermore, some bacterial genetic sequences are associated with instabilities that can interfere with standard industrial or laboratory practices, and might entail costly and burdensome quality control procedures.

The present invention also involves several methods for deleting genomic DNA from a genome without leaving any inserted DNA behind (scarless deletion). If one is making several sequential deletions from the single DNA molecule which makes up a bacterial genome, it is important not to leave any inserted DNA sequences behind. Such inserted sequences, if they were left behind, would be candidate sites for undesired recombination events that would delete uncharacterized and perhaps important portions of the remaining genome from the bacteria or cause other unanticipated genome rearrangements with untoward effects. Since one of the objectives of the genome reduction effort is to increase the genetic stability of the bacteria, leaving any inserted DNA behind would be contrary to the objective, and should be avoided. Thus the methods used to delete DNA from the genome become important and sophisticated.

In one aspect, the present invention relates to a bacterium having a genome that is genetically engineered to be smaller than the genome of its native parent strain. For exemplary purposes, the work described here has focused on the common laboratory and industrial bacterium Escherichia coli. The genome reduction work described here began with the laboratory E. coli strain K-12, which had prior to the work described here, a genome of 4,639,221 nucleotides or base pairs. The bacterium of the present invention can have a genome that is at least two percent (2%), in particular over five percent (5%), more particularly over seven percent (7%) to eight percent (8%) to fourteen percent (14%) to eighteen percent (18%) to twenty percent (20%), to forty percent (40%) to sixty percent (60%) smaller than the genome of its native parental strain. In particular, the genome is at least five percent (5%) and up to eight percent (8%), up to fourteen percent (14%), up to twenty percent (20%) or up to thirty percent (30%) smaller than the genome of a native parent strain. The reduced genome bacterium may also have a genome that is between 4.41 Mb and 3.71 Mb, between 4.41 Mb and 3.25 Mb or between 4.41 Mb and 2.78 Mb. The term "native parental strain" means a bacteria strain (or other organism) found in natural or native environment as commonly understood by the scientific community and on whose genome a series of deletions can be made to generate a bacterial strain with a smaller genome. The percentage by which a genome has become smaller after a series of deletions is calculated by dividing "the total number of base pairs deleted after all of the deletions" by "the total number of base pairs in the genome before all of the deletions" and then multiplying by 100.

Another aspect of the present invention comprises a reduced genome bacteria in which about 5% to about 10% of its protein coding genes are detailed. In particular, about 10% to 20% of the protein coding genes are deleted. In another embodiment of the invention, about 30% to about 40%) to about 60% of the protein encoding genes are deleted.

Generally speaking, the types of genes, and other DNA sequences, that can be deleted are those the deletion of which does not adversely affect the rate of survival and proliferation of the bacteria under specific growth conditions. Whether a level of adverse effect is acceptable depends on a specific application. For example, a 30% reduction in proliferation rate may be acceptable for one application but not another. In addition, adverse effect of deleting a DNA sequence from the genome may be reduced by measures such as changing culture conditions. Such measures may turn an unacceptable adverse effect to an acceptable one. In particular, the proliferation rate is approximately the same as the parental strain. However, proliferation rates ranging from about 5%, 10%, 15%, 20%, 30%, 40% to about 50% lower than that of the parental strain are within the scope of the invention. More particularly, particular doubling times of bacteria of the present invention may range from about thirty minutes to about three hours.

The bacteria of the present invention maybe engineered by the methods of the present invention to optimize their use of available resources (i.e., nutrients) for the production of desired products. Those products may be recombinant proteins, by way on non-limiting example insulin, interleukins, cytokines, growth hormones, growth factors, erythropoietin, colony stimulating factors, interferon, antibodies, antibody fragments, or any other useful recombinant protein. The recombinant product may be a therapeutic product, a vaccine component, a diagnostic product, or a research reagent. The bacteria may also be used as a background to express industrially useful products such as commercially useful metabolic intermediates and end products such as vanillin, shikimic acid, amino acids, vitamins, organic acids, and the like, and chemical compounds not naturally produced in the bacteria but produced as a result of metabolic pathway engineering or other genetic manipulation—(see, e.g., U.S. Pat. Nos. 6,472, 169 and 6,372,476, both of which are incorporated herein by reference).

Below, E. coli is used as an example to illustrate the genes and other DNA sequences that are candidates for deletion in order to generate a bacterium that can produce a desired product more efficiently. The general principles illustrated and the types of genes and other DNA sequences identified as candidates for deletion are applicable to other bacteria species or strains. It is understood that genes and other DNA sequences identified below as deletion candidates are only examples. Many other E. coli genes and other DNA sequences not identified may also be deleted without affecting cell survival and proliferation to an unacceptable level.

The native parent strain of the reduced genome bacterium may be any bacterial strain, as well as an intermediate strain from which the bacterium is derived. Representative examples of parent strains include, but are not limited to, E. coli strains such as K-12 or B, or a strain with a genome sequence substantially identical thereto. The E. coli K-12 strain may be a derivative strain including, but not limited to MG1655, DH10B, DH5α, Invα, Top10, Top10F, JM103, JM105, JM109, MC1061, MC4100, XL1-Blue, EC100 or EC300. E. coli B strains include REL606, BL/R and BL21 (DE3).

The nucleotide sequence of the genome of the parental strain may be partially or completely known. In particular, the entire sequence is available. Such complete or partial sequences are readily available in the Gen\\ database. The full genomic sequence of several strains of E. coli is, of course, now published (for example, Blattner et al., 1997, K-12 Strain MG1655; See also GenBank Accession No. U00096; Perna et al, 2001; Hayashi et al., 2001; and Welch et al., 2002, GenBank Accession No. AE014075, and GenBank Accession No. CP001509, all of which are incorporated herein by reference in their entirety), as is the sequence of several other commonly used laboratory bacteria. The nucleic acid sequence of E. coli MG1655 (annotated version m56), (NCBI accession no. U00096.1) is set forth in SEQ ID NO: 1 with a total size of 4,639,675 nucleotides or base pairs. To start the deletion process, the genome of the bacteria is analyzed to look for those sequences that represent good candidates for deletion. Of course, these techniques can also be applied to partially sequenced genomes in the genomic areas for which sequence date is available or could be determined.

In E. coli, and other bacteria as well, as well as in higher organisms, a type of DNA sequence that can be deleted includes those that in general will adversely affect the stability of the organism or of the gene products of that organism. Such elements that give rise to instability include transposable elements, insertion sequences, and other "selfish DNA" elements which may play a role in genome instability. For example, insertion sequence (IS) elements and their associated transposes are often found in bacterial genomes, and thus are targets for deletion. IS sequences are common in E. coli, and all of them may be deleted. For purposes of clarity in this document, the inventors use the term IS element and transposable element generically to refer to DNA elements, whether intact or defective, that can move from one point to another in the genome. An example of the detrimental effects of IS elements in science and technology is the fact that they can hop from the genome of the host E. coli into a BAC plasmid during propagation for sequencing. Many instance are found in the human genome and other sequences in the GenBank database. This artifact could be prevented by deletion from the host cells of all IS elements. For a specific application, other specific genes associated with genomic instability may also be deleted.

The deletion of all IS sequences from host cells (for example, E. coli) according to the present invention which, results in a "clean genome" as described above, provides a more genetically stable and useful cell. Additional DNA may be deleted from such a "clean genome" cell. The additional DNA to be deleted may be determined by the particular use for which the strain is intended. Such DNA may include, for example, DNA not required for cell survival and or growth.

Shown in FIG. 1 is illustration of the E. coli genome, which natively, in the K-12 strain, comprises 4,639,221 base pairs. FIG. 1, shows, on the inner ring, the scale of the base pair positions of the E. coli K-12 genome (strain MG1655), scaled without deletions (see also Blattner et al., supra). The next ring progressively outward shows regions of the K-12 genome that are missing or highly altered in a related strain O157:H7, and which are thus potentially detectable from the K-12 genome. The next ring outward shows the positions of the IS elements, both complete and partial, in the native genome. The next ring moving outward shows the positions of the RHS elements A to E and flagellar and restriction regions specially targeted for deletion here. The outermost ring shows the location of the deletions actually made to the genome, as also listed in Tables 1 and 2 below. These deletions make up about 14 percent of the base pairs in the original K-12 MG1655 genome. Using methods of the present invention 18% to 20% to about 40% of the genome will be deleted using the design paradigms described herein.

Another family of E. coli genes that can be deleted are the restriction modification system genes and other endogenous nucleases whose products destroy foreign DNA. These genes are not important for bacterial survival and growth in culture environments. These genes can also interfere with genetic engineering by destroying plasmids introduced into a bacterium. Positions of restriction modification system genes on an E. coli genome map are shown in FIG. 1 and Table 1. In one embodiment of the invention, other DNA methylase genes may be added back to the deleted E. coli strain so as to optimize the strain for certain uses, for example, eukaryotic methylase genes.

Another family of E. coli genes that can be deleted is the flagella gene family. Flagella are responsible for motility in bacteria. In natural environments, bacteria swim to search for nutrients. In cultured environments, bacteria motility is not important for cell survival and growth and the swimming action is metabolically very expensive, consuming over 1% of the cellular energy to no benefit. Thus, the flagella genes may be deleted in generating a bacterium with a smaller genome. Positions of flagella genes on an E. coli genome map are shown in FIG. 1 and Table 1.

One type of E. coli DNA element, already mentioned, that can be deleted is the IS elements (or transposable elements). IS elements are not important for bacteria survival and growth in a cultured environment and are known to interfere with genome stability. Thus, the IS elements can be deleted in generating a bacterium with a smaller genome. Positions of the IS elements on an E. coli genome map are shown in FIG. 1 and Table 1.

Another type of E. coli DNA element that can be deleted is the Rhs elements. All Rhs elements share a 3.7 Kb Rhs core, which is a large homologous repeated region (there are 5 copies in E. coli K-12) that provides a means for genome rearrangement via homologous recombination. The Rhs elements are accessory elements which largely evolved in some other background and spread to E. coli by horizontal exchange after divergence of *E. coli* as a species. Positions of the Rhs elements on an *E. coli* genome map are shown in FIG. 1 and Table 1.

One type of region in the *E. coli* genome that can be deleted is the non-transcribed regions because they are less likely to be important for cell survival and proliferation. Another type of regions in the *E. coli* genome that can be deleted is the hsd regions. The hsd regions encode for the major restriction modification gene family which has been discussed above. Positions of the non-transcribed regions and the hsd regions on an *E. coli* genome map are shown in FIG. 1 and Table 1.

Prophages, pseudogenes, toxin genes, pathogenicity genes, periplasmic protein genes, membrane protein genes are also among the genes that may be deleted, based on the gene selection paradigm discussed herein. After the sequence of *E. coli* K-12 (see Blattner, et al., supra), was compared to the sequence of its close relative O157:H7 (See Perna et al., supra) and it was discussed that 22% (K-12) and 46% (O157:H7) of the protein encoding genes were located on strain specific islands of from one to about 85 kb inserted randomly into a relatively constant backbone.

Prophages consist of viral DNA incorporated into the host bacterial genome. Over time, due to genome rearrangements and the like, the inserted viral DNA may become inactive, or cryptic, and lose the ability to produce active phage. Nevertheless, these cryptic prophages may retain the capacity for producing gene products that are deleterious to the host bacteria, particularly during periods of stress, during which cryptic prophage can reactivate. Prophage elements of special concern are genes encoding lysin and holin proteins that can compromise cellular integrity and viability if expressed. *E. coli* production strains typically contain approximately a dozen prophages. Positions of prophage elements on an *E. coli* genome map are shown at Table 1.

*E. coli* K12 strains cumulatively contain twelve prophages which comprise ~3.6% of the genome: CP4-6, DLP12, e14, phi80Lac, rac, Qin, CP4-44, P2*B/PR-X, CPS-53/KpLE1, CPZ-55, CP4-57/SsrA*B, and KpLE2. Each of these prophages may be partially or entirely deleted. Reduced genome strain MDS12 has all of the prophage elements of parent strain MG1655 deleted therefrom and all subsequently created strains (MDS13, MDS14, MDS15 . . . MDS40) also lack all prophage elements. Strain MDS40 (and all subsequently created strains) additionally lack all insertion sequences. The genetic position of each K12 prophage, as well as the first reduced genome strain from which each prophage was deleted, is listed below.

| Prophage | Genes | Location | Reduced Genome Strain |
|---|---|---|---|
| CP4-6 | b0245-b0281 | 262182-296489 | MD1 |
| DLP12 | b0537-b0565 | 564025-585326 | MD12 |
| e14 | b1137-b1159 | 1195443-1210646 | MD11 |
| rac | b1345-b1375 | 1409966-1433025 | MD2 |
| Qin | b1544-b1579 | 1630450-1646830 | MD8 |
| CP4-44 | b1994-b2006 | 2064181-2077053 | MD5 |
| PR-X | b2082-b2084 | 2165324-2166023 | MD37 |
| CPS-53 | b2349-b2363 | 2464404-2474619 | MD7 |
| CPZ-55 | b2442-b2450 | 2556791-2563352 | MD3 |
| CP4-57 | b2662-b2646 | 2753978-2776007 | MD4 |
| KpLE2 | b4271-b4308 | 4494108-4534178 | MD9 |

*E. coli* B strains contain all or a subset of eleven prophages: DLP12, X*B, RybB*B, Rac, Qin, CP4-44, P2*B/PR-X, CP4-57/SsrA*B, PheV*B, SelC*B and KpLE2. Each of these prophages may be partially or entirely deleted. Thus in one aspect, the present invention provides a reduced genome *E. coli* bacterium lacking all or a subset of prophage elements from these prophages. The genetic position of each BL21 (DE3) prophage is listed below.

| Prophage | Genes | Location | Reduced Genome Strain |
|---|---|---|---|
| DLP12 | ECD00486-ECD00513 | 533895-550997 | BL1 |
| Lambda DE3 | ECD10001-ECD10058 | 748396-791335 | |
| Rybb*B | ECD00815-ECD00851 | 872499-892617 | |
| rac | ECD01322-ECD01346 | 1397093-1410543 | |
| Qin | ECD01503-ECD05147 | 1581583-1597951 | |
| CP4-44 | ECD01903-ECD01909 | 1971307-1975275 | BL2 |
| SsrA*B/CP4-57 | ECD02509-ECD02152 | 2622524-2627371 | |
| Phev*B | ECD02797-ECD02811 | 2941466-2944376 | BL5 |
| Selc*B | ECD03516-ECD03540 | 3703770-3724679 | |
| KpLE2 | ECD04136-ECD04181 | 4408133-4445112 | |

A list of the prophages of several *E. coli* K12 and B strains is provided below:

| | *E. coli* B strains | | *E. coli* K12 strains | | | | |
|---|---|---|---|---|---|---|---|
| Prophage | REL606 | BL21(DE3) | DH10B | DH5a | Stabl3 | W3110 | MG1655 |
| CP4-6 | | | X | X | X | X | X |
| DLP12 | X | X | X | X | X | X | X |
| λ*B | X | X | | | | | |
| RybB*B | X | X | | | | | |
| e14 | | | | X | X | X | X |
| phi80Lac | | | X | X | | | |
| Rac | X | X | X | X | | X | X |
| Qin | X | X | X | X | X | X | X |
| CP4-44 | X | X | X | X | X | X | X |
| P2*B | X | | X | X | X | X | X |
| CPS-53 | | | X | X | X | X | X |
| CPZ-55 | | | X | | | | X |
| SsrA*B | X | X | X | X | | X | X |
| PheV*B | X | X | | | | | |
| SelC*B | X | X | | | | | |
| KpLE2 | X | X | X | X | X | X | X |
| Total | 11 | 10 | 11 | 11 | 8 | 10 | 11 |

In one aspect, the present invention provides a reduced genome *E. coli* bacterium lacking all or a subset of elements from these prophages. In a particular embodiment, the reduced genome *E. coli* lacks all lysin and holin genes from each of these prophages.

Among other genes that may be deleted are genes that encode bacteriophage receptors including, for example, tonA (FhuA) and/or its complete operon fhu ABC which encodes the receptor for the lytic phage T1.

One general method to identify additional genes and DNA sequences as deletion candidates is to compare the genome of one bacterial strain to one or more others strains. Any DNA sequences that are not present in two or three of the strains are less likely to be functionally essential and thus can be used for identifying candidates for deletion. In the examples described below, the complete genomic sequences of two *E. coli* strains, O157:H7 EDL933 and K-12 MG1655, were compared. DNA sequences that were not found in both strains were used to identify targets for deletion. Twelve such identified targets from *E. coli* strain MG1655 were deleted, resulting in a bacteria strain with a genome that is about 8% smaller. The bacteria with the reduced genome grow at substantially the same rate as the native parent MG1655 strain.

The DNA sequence of a uropathogenic *E. coli* strain CFT073 H7 (see Welch et al., supra), was recently determined and its sequence was compared to the K-12 (MG1655) and O157:H7. Results show that only about 40% of all coding genes found in any one of the genomes is present in all of the genomes and CFT073, K-12 and O157:H7 are composed of 67%, 43% and 68% strain specific island genes. Based on this information, as much as about 60% of the protein coding sequences may be deleted from *E. coli*. In particular, at least 5% or about 90% or about 15% or about 21% of the protein coding genes are deleted. More particularly, about 30% of the protein coding genes are deleted. It should be noted that there may be genes essential for growth in one strain that are not required for growth in other strains. In such cases, the gene essential for growth of that strain is not deleted from the strain or if deleted is replaced with another gene with a complementary function so as to permit growth of the strain.

In a particular embodiment of the invention, sequence information is used to select additional genes from (using the methods of the present invention) an *E. coli* genome so as to produce a genome of about 3.7 megabases (about 20% smaller than K-12) containing 73 deletions to remove about 100 "islands" and surrounding DNAs that will still allow for adequate growth of the strain when cultured on minimal media. The design also calls for complete elimination of any remaining transposable elements (IS sequences) from the genome.

Perisplasmic Cleansing and Protein Expression

For reasons discussed herein, there remains a need in the art for production of recombinant proteins which will be secreted into the periplasmic space of bacteria and the methods of the present invention provide for the engineering of bacteria to optimize periplasmic expression.

Gram-negative bacteria, such as *E. coli*, have two cellular membranes, the inner cell membrane and the outer cell membrane. Two membranes are separated by a periplasmic space (PS). Bacterial proteins with appropriate signal sequences are secreted through the inner cell membrane into the PS by at least two different systems, Sec-system and Tat-system. (Danese et al., 1998; Fekes et al., 1999; and Pugsley, 1993 (sic); Hynds et al., 1998; Santini et al., 1998; Sargent et al., 1998 (TAT) all of which are incorporated herein by reference.

The Sec-system recognizes an appropriate signal peptide and transports the protein, using cytoplasmic ATP and electronmotive force, into the periplasm in an unfolded state. After cleavage of the signal protein, the new protein folds with the aid of chaperones, peptidyl-prolyl isomerases, and a thioredoxin linked system which catalyses disulfide bond formation. See, e.g., Hynds et al., 1998; Santini et al., 1998; Sargent et al., 1998 (TAT), all of which are incorporated herein by reference.

In contrast to Sec-system, the Tat-system transports large proteins in fully folded conformation and is more specific in recognition of appropriate signal sequences. The inventors have selected the periplasm because (1) it is a particular site for expressing heterologous recombinant proteins, (2) for industrial use in controlled conditions, it has many unnecessary proteins, and (3) it plays a role in many unnecessary adaptation and control systems, some of which appear to be detrimental. By removing native proteins from the periplasm, the inventors anticipate that they will be able to greatly improve the process for protein production. Expression and secretion of proteins in the periplasm has been reviewed in Hanahan, 1983; Hockney, 1994; and Hannig et al., 1998, all of which are incorporated by reference.

There are several reasons why the periplasm is a good site for protein production; (1) it is possible to produce a recombinant protein with the amino terminus identical to the natural protein, whereas in the cytoplasm, proteins invariably begin with the amino acid methionine; (2) many proteins can fold correctly in the periplasmic space (3) the correct disulfide bonds can form in the oxidising environment of the periplasm; (4) the periplasmic space contains much less and far fewer proteins than the cytoplasm, simplifying purification (5) there are fewer proteases than in the cytoplasm, reducing protein digestion and loss; (6) expressed proteins can be readily released with other periplasmic proteins by specifically disrupting the outer membrane, substantially free of the more abundant cytoplasmic proteins. The periplasmic space has natural enzyme systems, linked to cellular cytoplasmic metabolism through the inner membrane, to undertake these processing tasks, presumably because this is the organelle in which most inner and outer membrane proteins are processed. By contrast, it has proven very difficult to obtain proper folding of recombinant protein chains expressed in the reducing environment of the cytoplasm. Often proteins aggregate into insoluble "inclusion bodies." Whilst initial inclusion body purification might be simpler, the proteins need to be re-dissolved and re-folded, a process that is unpredictable and difficult to control, and for some proteins, so inefficient as to be unworkable at industrial scale.

Recombinant proteins are generally produced in the periplasm by expressing fusion proteins in which they are attached to a signal peptide that causes secretion into the periplasmic space. There the signal peptide is cleaved off very precisely by specific signal peptidases. Second generation recombinant human growth hormone is manufactured by this method by Genentech (Nutropin, Full Prescriber Information.) and Pharmacia. Not all proteins can be successfully produced by this route and there is evidence that the secretion and post-secretion processing systems have limited capacity. Also, there are still protein contaminants to deal with. Notably, there is a warning on one such approved product, that it contains traces of *E. coli* periplasmic proteins that cause the production of antibodies in some patients (Gonotropin: Full Prescriber information). While it is claimed that this is not a problem in the clinic, it must be regarded as undesirable. The materials and methods of the present invention will allow the reduction or elimination of this problem.

There is need in the art for production of recombinant proteins which will be secreted into PS. This secretion may be accomplished by utilizing Sec- or Tat-systems or any other secreting pathogens available in the respective bacteria. In either case, the appropriate signal peptide will be added to the recombinant protein. If the Sec-system is to be used, than the following additional experiments are needed. Since there are reports that Sec-system can be saturated by high efficiency expression constructs, the first set of experiments will be to develop a system with optimum expression level of the recombinant protein which can be properly transported and folded in PS.

Recombinant DNA constructs useful for periplasmic expression in the reduced genome bacteria of the present invention comprise a first DNA sequence coding for a signal peptide capable of mediating transport of a protein to the periplasmic space operatively linked to at least a second DNA sequence coding for a desired heterologous protein. The signal sequence maybe native to the protein to be expressed. In particular, the protein transported into the periplasmic space is biologically active. Expression of the recombinant DNA construct may be under the control of an inducible promoter or a promoter that is constitutively expressed in the host bacterium. The use of inducible promoters is particularly advantageous when using the Sec system which is known to be saturable. For example, lac-based promoter/repressor, inducible by the non-metabolisable galactose derivative, IPTG, may be used. Such promoters allow fine tuning of expression and secretion through the Sec system thereby optimizing periplasmic expression.

The recombinant protein may also be co-expressed with chaperones/disulfide-bond forming enzymes to ensure proper folding of the recombinant protein. DNA sequences useful for periplasmic expression of recombinant protein include but are not limited to those described in U.S. Pat. Nos. 5,747,662; 5,578,464; 6,335,178; and 6,022,952. Thomas et al., 2001; Weiner et al., 1998; and *Current Protocols in Molecular Biology*, 1994, all of which are incorporated herein by reference in their entirety.

In one embodiment of the present invention, nine known and 3 putative periplasmic protein genes were successfully deleted in constructing MDS40, without significantly affecting the ability of the organism to grow on minimal medium. (See Table 4 and data below). These mutations affect a range of functions, including amino acid uptake, inorganic metabolism, cell membrane maintenance, sugar metabolism, and adhesion.

Approximately 85 genes have been deleted that code for known or putative membrane proteins, identified by their signal-peptide sequences. Of these 33 are involved in flagellar structure or biosynthesis; 9 are involved in fimbrial structure or biosynthesis; and 13 are involved in general secretory pathways. The remainder have a variety of known or putative functions in the cell membranes. Many of these proteins are believed to be processed in the periplasmic space. They have also been deleted in constructing MDS40, without significantly affecting the ability of the organism to grow on minimal medium.

By searching for signal peptide-like sequences in annotated MG1655 databases, and cross-relating these with the literature the inventors have identified 181 proteins that the majority of which are believed to be resident periplasmic proteins. A number of these proteins have been classified according to function into several groups excluding: adhesion and mobility; nutrient and salt uptake, trace element uptake; environmental sensing; defense and protection; and periplasmic protein secretion and processing. Among the genes or full operons which have been or will be deleted are those coding for sugar and amino acid transport proteins, unlikely to be needed in defined minimal media say for biopharmaceutical production.

To monitor efficiency of the recombinant protein transportation into PS, either of three commercially available tags: *E. coli* alkaline phosphatase, *Aequoria* green fluorescent protein (GFP) or human growth hormone protein may be used according to the methods described above. The human growth hormone protein is useful for final demonstration purposes and will be used in ELISA and gene chip-based measurements of the recombinant protein localization to PS.

One can test the consequence of deleting one or several genes or other DNA sequences from the genome. For example, after one or several genes or other DNA sequences of the genome have been deleted, one can measure the survival and proliferation rate of the resultant bacteria. Although most of the above-identified genes or other DNA sequences may be deleted without detrimental effect for purpose of producing a desired product, it is possible that the deletion of a specific gene or other DNA sequence may have an unacceptable consequence such as cell death or unacceptable level of reduction in proliferation rate. This possibility exists because of redundancies in gene functions and interactions between biological pathways. Some deletions that are viable in a strain without additional deletions will be deleterious only in combination with other deletions. The possibility exists also because of certain methods used to identify deletion candidates. For example, one method used to identify deletion candidates is to compare two *E. coli* strains and select genes or other DNA sequences that are not present in both strains. While the majority of these genes and other DNA sequences are not likely to be functionally essential, some of them may be important for a unique strain. Another method used to identify deletion candidates is to identify non-transcribed regions and the possibility exists that certain non-transcribed regions may be important for genome stability.

The consequence of deleting one or several genes or other DNA sequences to be tested depends on the purpose of an application. For example, when high production efficiency is the main concern, which is true for many applications, the effect of deletions on proliferation rate and medium consumption rate can be the consequence tested. In this case, the consequence tested can also be more specific as the production speed quantity and yield per cell of a particular product. When eliminating native protein contamination is the main concern, fewer native proteins and lower native protein levels, or the absence of a specific native protein, can be the consequence tested.

Testing the consequence of deleting a gene or other DNA sequence is important when little is known about the gene or the DNA sequence. Though laborious, this is another viable method to identify deletion candidates in making a bacterium with a reduced genome. This method is particularly useful when candidates identified by other methods have been deleted and additional candidates are being sought.

When the consequence of deleting a gene or other DNA sequence has an effect on the viability of the bacteria under a set of conditions, one alternative to not deleting the specific gene or other DNA sequence is to determine if there are measures that can mitigate the detrimental effects. For example, if deleting lipopolysaccharide (LPS) genes results in poor survival due to more porous cellular membranes caused by the absence from the cellular membranes of the transmembrane domain of the LPS proteins, culture conditions can be changed to accommodate the more porous cellular membranes so that the bacteria lacking the LPS genes can survive just as well as the bacteria carrying the LPS genes.

Methods for deleting DNA sequences from bacterial genomes that are known to one of ordinary skill in the art can be used to generate a bacterium with a reduced genome. Examples of these methods include but are not limited to those described in Posfai et al., 1997; Muyrers et al., 1999; Datsenko et al., 2000; and Posfai et al., 1999, all of which are hereby incorporated by reference in their entirety. Basically, the deletion methods can be classified to those that are based on linear DNAs and those that are based on suicide plasmids. The methods disclosed in Muyrers et al., 1999 and Datsenko et al., 2000, are linear DNA-based methods and the methods disclosed in Posfai et al., 1997 and Posfai et al., 1999, are suicide plasmid-based methods.

Some known methods for deleting DNA sequences from bacterial genomes introduce extraneous DNA sequences into the genome during the deletion process and thus create a potential problem of undesired homologous recombination if any of the methods is used more than once in a bacterium. To avoid this problem, scarless deletion methods are used. By scarless deletion, the inventors mean a DNA sequence is precisely deleted from the genome without generating any other mutations at the deletion sites and without leaving any inserted DNA in the genome of the organism. However, due to mistakes, such as those made in PCR amplification and DNA repairing processes, one or two nucleotide changes may be introduced occasionally in scarless deletions. Described below are some novel scarless deletion methods, either linear DNA-based or suicide plasmid-based. These novel methods have been applied to E. coli strains in the examples described below. It is understood that the specific vectors and conditions used for E. coli strains in the examples can be adapted by one of ordinary skill in the art for use in other bacteria. Similar methods and plasmids can be used to similar effect in higher organisms. In some instances it may be more appropriate to modify an existing production strain rather than transfer production to the minimized genome E. coli strain.

The methods of the present invention are not limited to use in reducing the genome of bacteria, for example, the present methods may be used to delete DNA from bacteriophage such as P1, P2, lambda and other bacteriophage. Such methods permit the engineering of bacteriophage genomes so as to improve their useful properties and/or to decrease or eliminate certain properties which impair the use of such bacteriophage for a variety of purposes. Similarly, the methods of the present invention are useful for modifying plasmids that reside in bacteria so as to eliminate harmful elements (e.g., virulence genes) from the plasmid and to improve other useful properties of the plasmids.

The well known generalized transducing bacteriophage P1 has been as described above for transducing pieces of DNA into recipient E. coli. Certain gene features of P1, however, ultimately limit the capacity to pick up and package genomic DNA for transduction. In particular, the packaging site (pac) site of P1 is a GATC rich region which when methylated by the dam methylase of P1 limits the amount of genomic DNA into the phage coat. However in the absence of dam associated methylation of the packaging site, packaging of DNA becomes "sloppy," that is, it more readily packages portions of genomic DNA than would be the case if the packaging site were methylated. Therefore, it would be advantageous to engineer the P1 genome to remove dam gene using the deletion methods of the present invention thereby enhancing the ability to pick up and package genomic material.

Another drawback associated with the use of P1 transduction in that the phage carries two insertion sequences. On insertion sequence, IS1 is found between ssb and the prt loci of the P1 genome. Another, IS5 is in the res gene As a result, it is possible that when P1 is used in transduction that one or more of the insertion sequences could end up jumping into a genomic locus of the organism. Therefore, it would be advantageous to engineer the P1 genome to delete the IS sequences using the methods of the present invention thereby preventing genomic contamination where P1 is used as a transduct.

In the above description, the present invention is described in connection with specific examples. It will be understood that the present invention is not limited to these examples, but rather is to be construed to be of spirit and scope defined by the appended claims.

Among the embodiments of the present invention is a *Shigella flexneri* having a reduced genome. Recently, the complete genome sequence of *Shigella flexneri* 2a strain 2457T was determined (the sequenced strain was redeposited at the American Type Culture Collection, as accession number ATCC 700930). The genome of *S. flexneri* consists of a single-circular chomosome of 4,599,354 base pairs (bp) with a G+C content of 50.9%. Base pair 1 of the chromosome was assigned to correspond with base pair one of *E. coli* K-12 since the bacteria shows extensive homology. The genome was shown to about 4082 predicted genes with an average size of 873 base pairs. The *S. flexneri* genome exhibits the backbone and island mosaic structure of *E. coli* pathogens albeit with much less horizontally transferred DNA and lacks 357 genes present in *E. coli* (see, Perna et al., 2001). The organism is distinctive in its large complement of insertion sequences, several genomic rearrangements, 12 cryptic prophages, 372 pseudogenes, and 195 *Shigella* specific genes. The completed annotated sequence of *S. flexneri* was deposited at GenBank accession number AE014073 which is incorporated herein by reference (see also "Complete Genome Sequence and Comparative Genomics of *Shigella flexneri* Serotype 2A strain 2457T", Wei et al., submitted for publication). It is striking to note that based on its DNA sequence, *Shigella* is phylogenetically indistinguishable from *E. coli*.

As is readily apparent from this disclosure, having the *S. flexneri* sequence in hand, its genome may be readily reduced using the methods and gene selection paradigms discussed herein. A reduce genome *Shigella* may be useful for the expression of heterologous (recombinant) proteins or other useful nutrients for reasons discussed herein with respect to reduced genome *E. coli* (live vaccine). Another use for reduced genome *Shigella* or for that matter any pathogenic bacteria susceptible to the deletion methods of the present invention is as a vehicle for the display or presentation of antigens for the purpose of inducing an immune response from a host. Such an engineered *Shigella* could, for example, have genes responsible for virulence deleted from the organism while maintaining other genes such as those encoding antigenic determinants sufficient to induce an immune response in a host and particularly a mucosal immune response in the intestinal wall of a host.

*Shigella flexneri* is potentially well suited for this strategy in that its virulence determinants have been characterized and have been localized to a 210-kb "large virulence (or Invasion) plasmid" whose nucleotide sequence has been determined and has been deposited as GenBank Accession No. AF348706 which is incorporated herein by reference (see also Venkatesan et al., 2001). Among the likely candidates for deletion from the Invasion plasmid is the cadA gene which encodes lysine decarboxylase.

The deleted *Shigella* invasion plasmid may be introduced into a reduced genome *E. coli* thereby allowing efficient expression of certain *Shigella* invasion plasmid genes capable of giving rise to an immune response in a host inoculated with the *E. coli*. The invasion plasmid may also be engineered to delete harmful genes from the plasmid such as the genes responsible for vacuole disruption. Particular candidate genes for removal from the invasion plasmid include one or more genes selected from the group consisting of ipaA, ipaB, ipaC, ipaD and virB. The present invention also allows the addition of other genes to the reduced genome-*E. coli* into which the invasion plasmid has been introduced so as to optimize expression of genes from the introduced, modified invasive plasmid.

The present invention is also directed to live vaccines comprising a reduced genome, for example, *E. coli*, or a reduced genome, for example, *E. coli* into which has been introduced genes encoding antigens capable of inducing an immune response in a host who has been inoculated with the vaccine. Reduced genome vaccines may be DNA based vaccines in containing a DNA known to be capable of inducing a desired physiological response in a hose (i.e., immune response).

One of the major advantages of a reduced genome organism according to the present invention is to provide a clean, minimal genetic background into which DNAs may be introduced to not only allow expression of a desired molecule, but it also affords the opportunity to introduce additional DNAs into the clean background to provide a source of molecules capable of optimizing expression of the desired product.

Deletion Methods
Construction of a Linear Targeting DNA

An example of the construction of a linear target DNA is as follows: To generate primer a+b (FIG. 1), 20 pmol of primer a was mixed with 20 pmol of primer b and PCR was performed in a total volume of 50 µl. Cycle parameters were: 15×(94° C. 40 sec/57° C. or lower [depending on the extent of overlap between primers a and b] 40 sec/72° C. 15 sec). Next 1 µl of this PCT product was mixed with 20 pmol of primers a and c (FIG. 1) each, 50 ng of pSG76-CS template and a second round of PCT was performed in a volume of 2×50 µl. cycle parameters were: 28×(94° C. 40 sec/57° C. 40 sec/72° C. 80 sec). The resulting, PCR-generated linear DNA-fragment was purified by Promega Wizard PCT purification kit, and suspended in 20 µl water. Elimination of the template plasmid (e.g., by DpnI digestion) is not needed. pSG76-CS serves as a template plasmid to generate linear targeting fragments by PCT. It contains the chloramphenicol resistance (CmR) gene and two I-SceI sites, and was obtained by the PCT-mediated insertion of a second I-SceI sites, and was obtained by the PCT-mediated insertion of a second I-SceI recognition site into pSG76-C, downstream of the NotI site. The two I-SceI sites are in opposite orientation.

Novel Linear DNA-Based Scarless Deletion Method I

Figure 2:
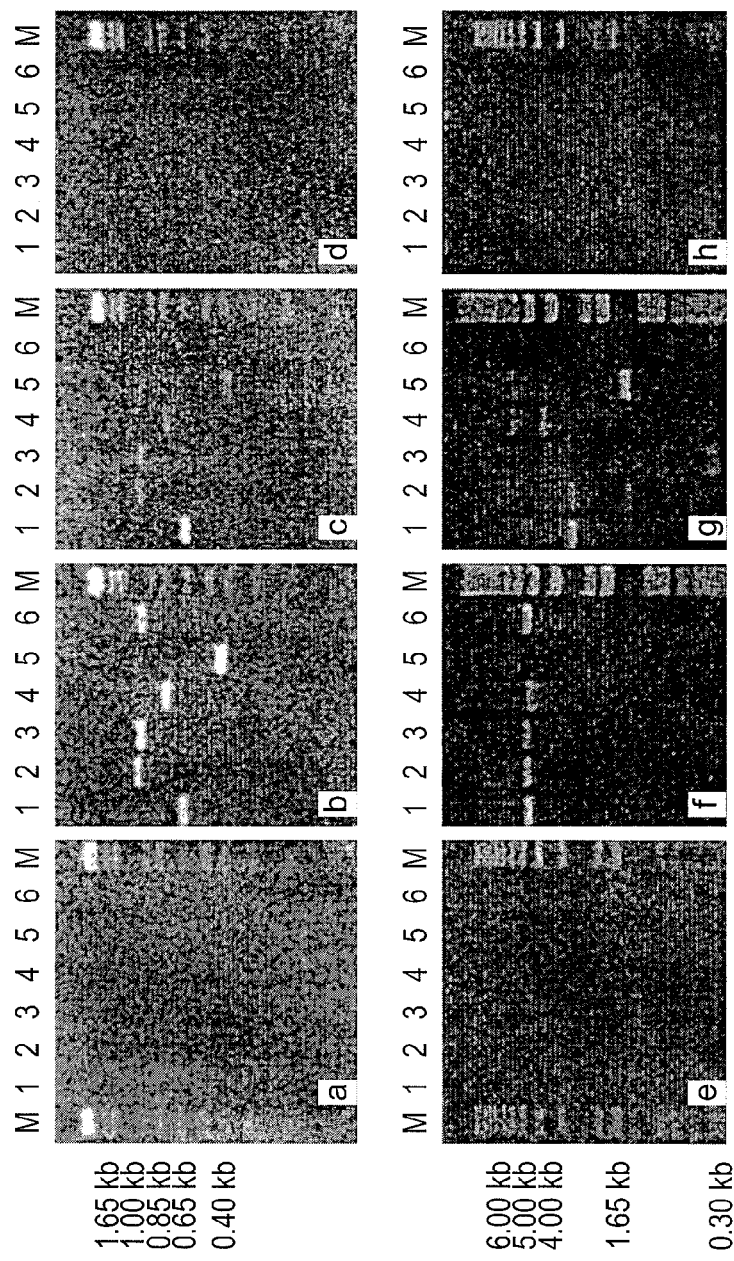
FIG. 2 illustrates a specific example of a linear DNA-based scarless genetic modification method of the present invention.

The novel DNA-based scarless deletion method of the present invention can be best understood when the following description is read in view of FIG. 2. Generally speaking, the method involves replacing a segment of the genome, marked for deletion, with an artificial DNA sequence. The artificial sequence contains one or more recognition sites for a sequence-specific nuclease such as I-SceI, which cuts at a sequence that does not occur natively anywhere in the *E. coli* K-12 genome. Precise insertion of the linear DNA molecule into the genome is achieved by homologous recombination aided by a system that can increase the frequency of homologous recombination. When the sequence-specific nuclease is introduced into the bacteria, it cleaves the genomic DNA at the unique recognition site or sites, and only those bacteria in which a homologous recombination event has occurred will survive.

Referring specifically to FIG. 2, the plasmid pSG76-CS is used as a template to synthesize the artificial DNA insert. The artificial insertion sequence extends between the sequences designated A, B and C in FIG. 2. The $C^R$ indicates a gene for antibiotic resistance. The insert DNA is PCR amplified from the plasmid and electroporated into the *E. coli* host. The insert was constructed so that the sequences A and B match sequences in the genome of the host which straddle the proposed deletion. Sequence C of the insert matches a sequence in the host genome just inside sequence B of the host genome. Then the bacteria are selected for antibiotic resistance, a selection which will be survived only by those bacteria in which a homologous recombination event occurred in which the artificial DNA inserted into the bacterial genome. This recombination event occurs between the pairs of sequences A and C. The inserted DNA sequence also includes a sequence B, now positioned at one end of the insert, which is designed to be homologous to a sequence in the genome just outside the other end of the insert, as indicated in FIG. 2. Then, after growth of the bacteria, the bacteria is transformed with a plasmid, pSTKST, which expresses the I-SceI sequence-specific nuclease. The I-SceI enzyme cuts the genome of the bacteria, and only those individuals in which a recombination event occurs will survive. 10-100% of the survivors are B to B recombination survivors, which can be identified by a screening step. The B to B recombination event deletes the entire inserted DNA from the genome, leaving nothing behind but the native sequence surrounding the deletion.

To repeat, the first step of the method involves providing a linear DNA molecule in a bacterium. The linear DNA molecule contains an artificial linear DNA sequence that has the following features: one end of the linear DNA sequence is a sequence identical to a genome sequence on the left flank of the genome region to be deleted, followed by a sequence identical to a genome sequence on the right flank of the genome region to be deleted; the other end of the linear DNA molecule is a sequence identical to a genome sequence within the genome region to be deleted; between the two ends of the linear DNA, there is a recognition site that is not present in the genome of the bacterial strain and an antibiotic selection gene. The artificial DNA sequence can be made using polymerase chain reaction (PCR) or directed DNA synthesis. A PCR template for this purpose contains the unique recognition site and the genomic DNA sequences on both ends of the artificial linear DNA sequence are part of the primers used in the PCR reaction. The PCR template can be provided by a plasmid. An example of a plasmid that can be used as a template is pSG76-C (GenBank Accession No. Y09893), which is described in Posfai et al. (1997). pSG76-CS (GenBank Accession No. AF402780), which is derived from pSG76-C, may also be used. pSG76-CS contains the chloramphenicol resistance ($Cm^R$) gene and two I-SceI sites, and was obtained by the PCR-mediated insertion of a second I-SceI recognition site into pSG76-C, downstream of the NotI site. The two I-SceI sites are in opposite direction.

An artificial or constructed DNA sequence can be provided to a bacterium by directly introducing the linear DNA molecule into the bacterium using any method known to one of ordinary skill in the art such as electroporation. In this case, a selection marker such as an antibiotic resistance gene is engineered into the artificial DNA sequence for purpose of selecting colonies containing the inserted DNA sequence later. Alternatively, a linear DNA molecule can be provided in a bacterium by transforming the bacterium with a vector carrying the artificial linear DNA sequence and generating a linear DNA molecule inside the bacterium through restriction enzyme cleavage. The restriction enzyme used should only cut on the vector but not the bacterial genome. In this case, the artificial linear DNA sequence does not have to carry a selection marker because of the higher transformation efficiency of a vector so that a bacterium with the inserted linear DNA can be screened by PCR later directly.

The second step of the scarless deletion method involves replacement of a genomic region by insertion of the artificial DNA molecule. The bacterial cells are engineered to contain a system that increases the frequency of homologous recombination. An example of such a system is the Red recombinase system. The system can be introduced into bacterial cells by a vector. The system helps the linear DNA molecule to replace a genomic region which contains the deletion target. As described in the examples below, a vector carrying a homologous recombination system that can be used in *E. coli* is pBADαβγ, which is described in Muyrers et al. (1999). Another plasmid pKD46 described in Datsenko et al. (2000) may also be used. Other plasmids that can be used include pGPXX and pJGXX. pGPXX is derived from pBADαβγ by replacing the origin of replication in pBADαβγ with pSC101 origin of replication. pJGXX is a pSC101 plasmid that encodes the Red functions from phage 933W under tet promoter control The third step of the scarless deletion method involves removal of the inserted DNA sequence. An expression vector for a sequence-specific nuclease such as I-SceI that recognizes the unique recognition site on the inserted DNA sequence is introduced into the bacteria. The sequence-specific nuclease is then expressed and the bacterial genome is cleaved. After the cleavage, only those cells in which homologous recombination occurs resulting in a deletion of the inserted linear DNA molecule can survive. Thus, bacteria with a target DNA sequence deleted from the genome are obtained. Examples of sequence-specific nuclease expression vectors that can be used in *E. coli* include pKSUC1, pKSUC5, pSTKST, pSTAST, pKTSHa, pKTSHc, pBADScel and pBADSce2. The sequence-specific nuclease carried by these vectors is I-SceI. pKSUC1, pKSUC5, pSTKST and pSTAST are described below in the examples.

The method described above can be used repeatedly in a bacterium to generate a series of deletions. When the expression vector for the homologous recombination system and the expression vector for the unique sequence-specific nuclease are not compatible with each other, such as the case for pBADαβγ and pKSUC1, transformation of the two vectors have to be performed for each deletion cycle. Transformation of the two vectors can be avoided in additional deletion cycles when two compatible plasmids, such as pBADαβγ and pSTKST, or pKD46 and pKSUC5, are used. An example of using two of these vectors that are compatible with each other is described in the examples below.

The above scarless deletion method can be modified to make a series of deletions on a bacterial genome more efficient (an example of which is Procedure 4 in Examples below). The first step of the modified method involves making insertions of a linear DNA molecule individually in bacterial cells, particularly wild-type bacteria cells, in a parallel fashion, resulting in a set of strains, each carrying a single insertion. This step can be carried out as described above. The second step of the modified method involves sequentially transferring individual insertions into the target cell whose genome is to be reduced. P1 transduction is an example of the methods that can be used for transferring insertions. The third step of the modified method involves recombinational removal of the inserted sequence, which can be carried out as described above.

Novel Linear DNA-Based Scarless Deletion Method II

In this novel linear DNA-based method, two DNA sequences, one of which is identical to a sequence that flanks one end of a bacterial genome region to be deleted and the other of which is identical to a sequence that flanks the other end of the bacterial genome region and oriented similarly, are engineered into a plasmid vector. The vector is herein termed the target vector. The two DNA sequences are located next to each other on the target vector. At least one recognition site for an enzyme that will only cut the target vector but not the bacterial genome is also engineered into the target vector at a location outside the two DNA sequences. The recognition site can be one for a sequence-specific nuclease such as I-SceI. The recognition site can also be one for a methylation-sensitive restriction enzyme that only cuts an unmethylated sequence. Since the recognition site, if there is any, on the bacterial genome is methylated, the restriction enzyme can only cut the target vector. The target vector is transformed into a bacterium and a linear DNA molecule is generated inside the bacterium by expressing in the bacterium the enzyme that recognizes and cuts the recognition site on the target vector. Next, a system that can increase homologous recombination is activated inside the bacterium to induce homologous recombination between the homologous sequences of the linear DNA and the bacterial genome that flank the region to be deleted. A bacterium with a targeted genome region deleted can be obtained as a result of the above homologous recombination.

This novel linear DNA-based method can also be used to replace a region of a bacterial genome with a desired DNA sequence. In this case, a desired DNA sequence that can undergo homologous recombination with the bacterial genome to replace a region on the genome is engineered into the target vector. All other aspects are the same as described above for deleting a region of the bacterial genome.

Regardless whether the method is used to delete or replace a target region in the bacterial genome, a marker gene for selecting incorporation of DNA carried on the target vector into the bacterial genome is not necessary due to the high incorporation efficiency. Simply screening 30-100 colonies by PCR usually allows the identification of a clone with desired modification in the bacterial genome.

Figure 3A:
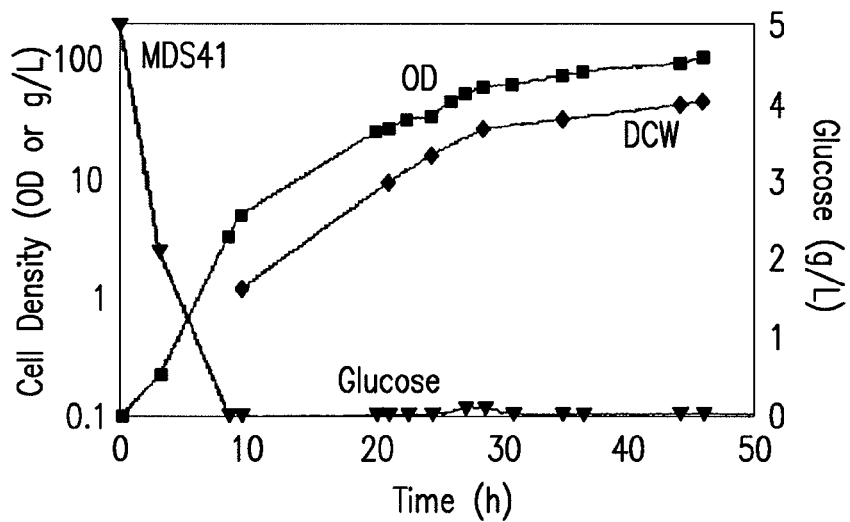
FIGS. 3A-B illustrate specific examples of another linear DNA-based method of the present invention.
Figure 3B:
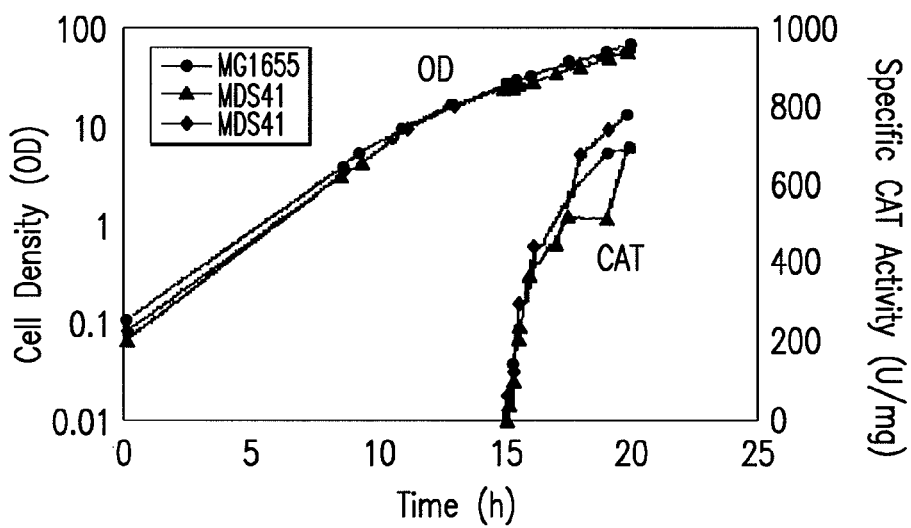
Figure 4A:
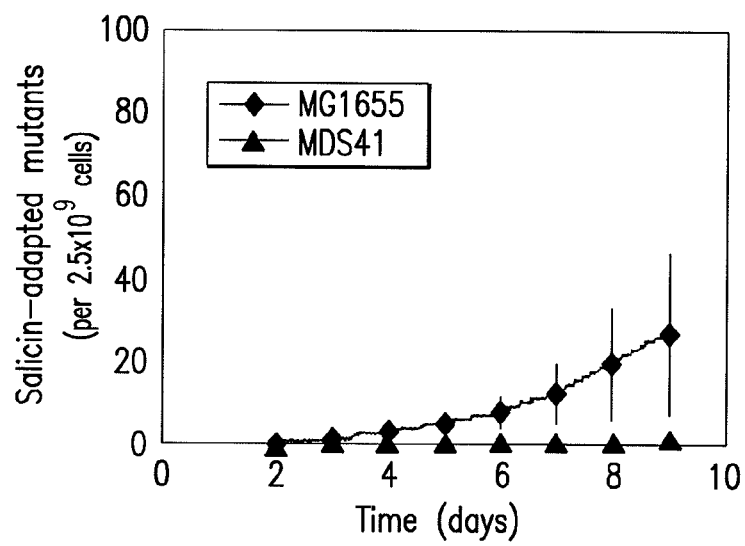
FIGS. 4A-B show a mutagenesis plasmid that can be used in the linear DNA-based method illustrated in FIGS. 3A-B.
Figure 4B:
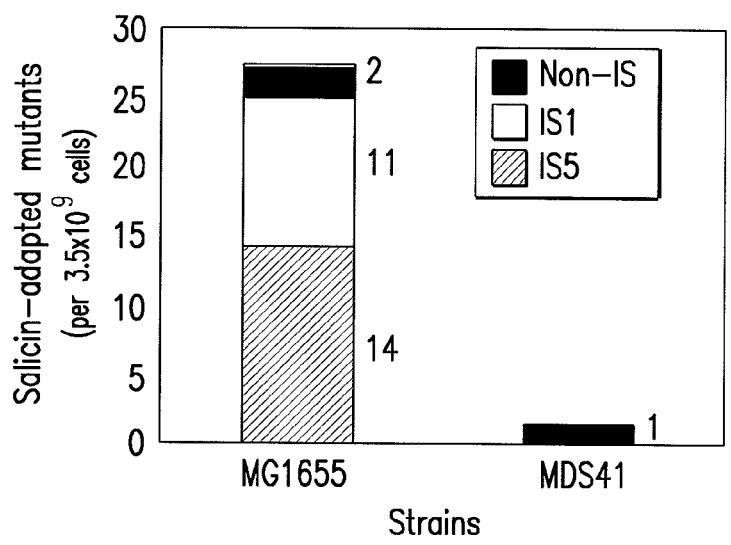

As a specific example, FIGS. 3 and 4 illustrates using this method for introducing an Amber stop codon in the middle of a gene. As a first step, a DNA fragment with the desired modifications located near the middle of the gene or chromosomal region is produced. A sequence-specific nuclease I-SceI recognition site is introduced at one side of the DNA fragment. This can be easily accomplished by including the sequence in the 5' end of PCR primers used to amplify the DNA fragment. Longer DNA fragments (500-5,000 nucleotides) generally work the best.

The DNA fragment is cloned into a multi-copy target plasmid vector such as pUC19 (GenBank accession No. M77789). Since this target vector is used along with a mutagenesis vector as described below, the target vector is engineered to be compatible with p15A origin plasmids (pACYC184-derived; GenBank accession No. X06403) and has a drug resistance marker other than chloramphenicol. These restrictions can be easily avoided by using an alternate mutagenesis plasmid.

As illustrated in FIG. 4, the mutagenesis plasmid used in this example contains the sequence-specific nuclease I-SceI and the lambda red genes exo, beta and gam under control of the P-BAD promoter. The plasmid also contains p15Aori and chloramphenicol resistance gene.

The target and the mutagenesis plasmids are transformed into a recA positive *E. coli*. The bacteria are selected for resistance to chloramphenicol and the resistance carried on the target plasmid. A single colony is then picked and cultured at 37° C. for about 7.0 hours in 1 ml of Rich Defined Media (Neidhardt et al., 1974, which is hereby incorporated by reference in its entirety) containing 0.2% arabinose and chloramphenicol. A series of dilutions (for example, 1:1,000, 1:10,000 and so on) of cultures is then plated on a non-selective medium such as LB. Next, the colonies are screened for desired mutations. If a growth phenotype is known, the screening can be done by patching on appropriate media. Otherwise, the screening is done with colony PCR followed by restriction digestion and electrophoresis or by sequencing.

Suicide Plasmid-Based Method

The suicide plasmid-based method described here can be used for both scarless gene deletion and gene replacement. The basic element of the method involves a plasmid vector named Interlock plasmid that contains an antibiotic resistance gene and a replication origin under the control of a promoter. The Interlock plasmid also contains one or more sites at which a DNA insert can be inserted. When the method is used for scarless deletion, the DNA insert includes two DNA sequences located right next to each other, oriented similarly, one of which is identical to a sequence that flanks one end of a bacterial genome region to be deleted and the other of which is identical to a sequence that flanks the other end of the bacterial genome region. When the method is used for gene replacement, the DNA insert includes a sequence that will replace a segment of a bacterial genome. When the promoter that controls the origin of replication is turned off, the replication of the plasmid is shut down and the antibiotic pressure can be used to select for chromosomal integrations at the site of the flanking region. After chromosomal integration at the site of the flanking region, the promoter that controls the replication origin from the plasmid can be turned on and the only bacteria that can survive are those in which a recombination event has occurred to eliminate said origin of replication, its promoter or both. When the DNA insert is for making scarless deletion, recombination between the integrated insert and the corresponding region in the genome will result in bacteria that either have the desired scarless deletion or the same genome before any integration. When the DNA insert is for gene replacement, recombination will result in bacteria that either have the desired replacement or the same genome before any integration. A screening step can then be performed to identify those bacteria with desired modifications in the genome.

A variation of the above method involves the same Interlock plasmid except that the plasmid also contains a sequence-specific nuclease recognition site that is absent in the bacterial genome. After chromosomal integration, instead of activating the origin of replication control promoter to select for recombination events, the bacteria are engineered to express the sequence-specific nuclease to cut the bacterial genome and select for recombination events.

The suicide plasmid-based method can also be used repeatedly in a similar fashion as the novel liner DNA-based methods described above to generate a series of deletions on a bacterial genome.

Figure 5:
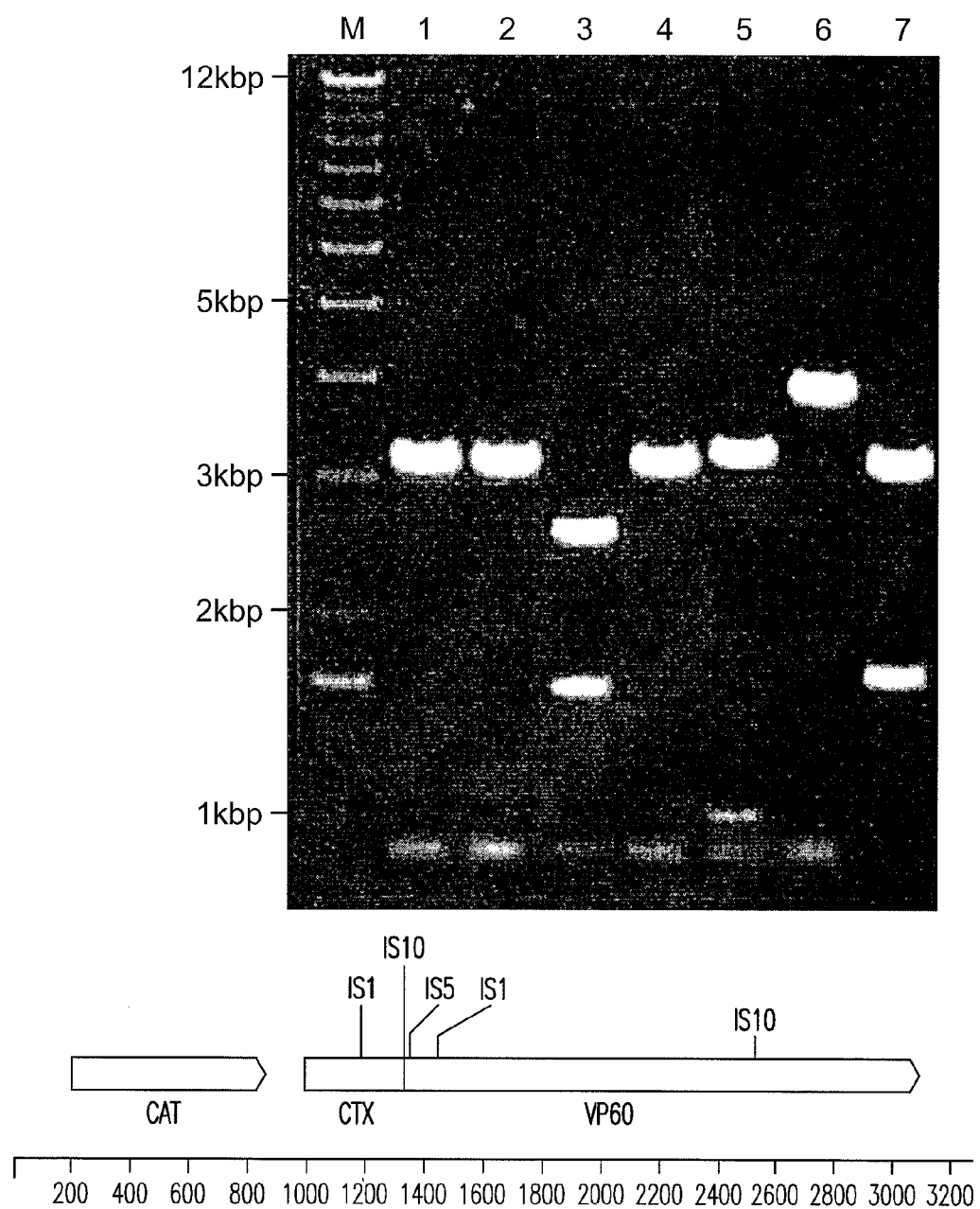
FIG. 5 illustrates a specific example of a suicide plasmid-based method of the present invention.
Figure 6:
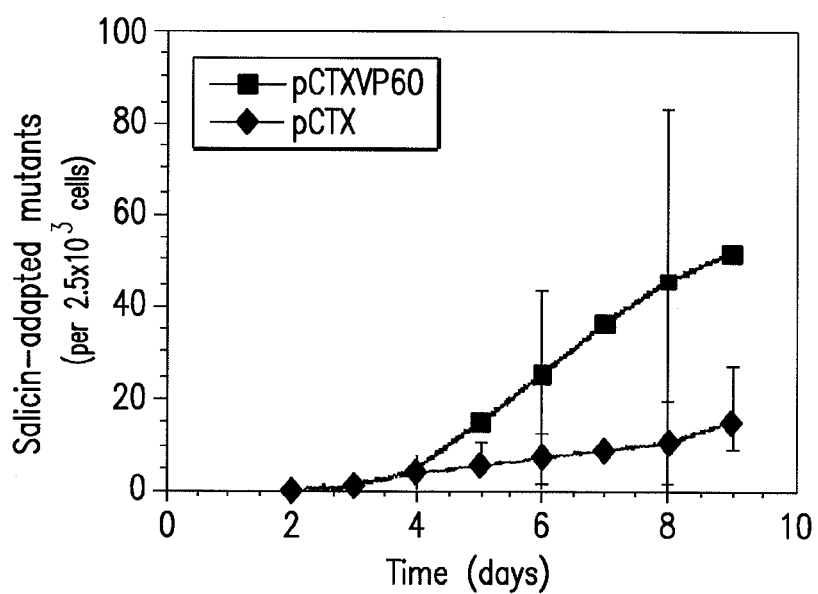
FIG. 6 shows three plasmids that can be used in the suicide plasmid-based method illustrated in FIG. 5.

FIG. 6 shows plasmid embodiments that can be used in the suicide plasmid-based method. pIL1 is an Interlock plasmid and pBAD-Sce-1 is a plasmid for expressing a sequence-specific nulcease I-SceI. pIL4 is a combination of both. The tet promoter used in pIL1 and pIL4 is tightly regulated and thus has advantages over other control mechanisms such as a temperature sensitive element which is more leaky. An example of using pIL4 for gene replacement is shown in FIG. 5 to illustrate the suicide plasmid-based method of the present invention. FIG. 5 shows that the insertion of a DNA insert into pIL4 and integration of pIL4 into the bacterial genome. With heat activated chlortetracycline (CTC), tet repressor is inactive, the 0 and P promoter is functional, and the plasmid replicates. After removing CTC, tet repressor binds the promoter for 0 and the P promoter and the replication is blocked. Chloramphenicol resistance can be used to select for integrants. FIG. 5 shows using the induction of the ectopic origin to select for homologous recombination and two possible outcomes of the homologous recombination. FIG. 5 shows the alternative way of selecting for homologous recombination and the two possible outcomes of the recombination. This alternative way involves inducing I-SceI expression to generate double-strand break.

Two specific embodiments of the suicide plasmid-based method are described below as protocol 1 and protocol 2. Either pIL1 or pIL4 can be used for protocol 1, and pIL1 in combination with pBAD-Sce-1 can be used for protocol 2. One of ordinary skill in the art can also adapt protocol 2 for using pIL4 alone.

Protocol 1 (Counterselection with Lambda Origin):

1. Generate the desired genomic modification as a linear DNA fragment. In the case of making an Amber mutant, the modification can be made by megaprimer PCR. To make a deletion in the genome, a fusion of the desired endpoints of the deletion should be used. The ends of the DNA fragment should be phosphorylated for cloning.
2. Create a blunt cloning site by digesting the pIL4 vector (FIGS. 5A and 6) with the restriction enzyme Srf1. Dephosphorylate the vector.
3. Perform a blunt ligation of the desired modification and the pIL4 vector.
4. (Note: this step is potentially dispensable in high throughput implementation.) Transform the ligation into a cloning strain of *E. coli* (such as JS5). Outgrow the transformation for 1 hour in LB+1 µg/ml cTc (cTc—chlortetracycline freshly autoclaved in LB media. A stock of 100 µg/ml is autoclaved for 20 minutes and then stored in the dark at 4° C. It can be used for up to 5 days. Alternately, a solution of 2 ng/ml of anhydrotetracycline can be substituted). Then plate on LB+Chloramphenicol (Cam 25 µg/ml)+cTc (1 µg/ml), and grow overnight at 37° C. Grow colonies in equivalent media and prepare plasmid miniprep DNA. Analyze by gel electrophoresis and select a clone with an insert.
5. Transform the verified plasmid into a recA positive strain of *E coli* (such as MG1655). Outgrow for 1 hour in LB+1 µg/ml cTc. Plate a portion of the outgrowth on plates containing Cam and 1 µg/ml cTc. Grow overnight at 37° C.
6. Pick a colony into 1 ml LB and plate 10 µl on a Cam plate. Grow overnight at 37° C.
7. Streak a colony on a Cam plate to be sure that every cell present contains the integrated plasmid. Grow overnight at 37° C.
8. Pick a colony into 1 ml LB and plate 100 µl of a 1:100 dilution on plates containing 5 µg/ml cTc. Grow overnight at 37° C.
9. (Screen for mutant) Only a fraction of the counterselected colonies will contain the desired modification and the others will be reversions to wt. The proportion of mutant to revertant will depend on the location of the modification in the cloned fragment. Some kind of screen must be performed to identify the desired mutant. For the production of Amber mutants, the gene in question can be amplified by PCR and digested with BfaI restriction enzyme (BfaI cuts Amber codons that are preceded by a 'C').

Protocol 2 (High Thruput Counterselection with I.SceI):
1-4 Same as protocol 1.
5. Co-transform the insert-carrying Interlock plasmid and pBAD-SceI into a recA positive strain of E coli (such as MG 1655). Outgrow for 1 hour in LB+1 ug/ml cTc. (Alternatively, the insert-carrying Interlock plasmid can be transformed on it's own into competent cells already carrying pBAD-SceI).
6. Add Chlorampehnicol to 25 μg/ml and Kanamycin to 50 μg/ml. Grow for 1-2 hours at 37° C. with shaking.
7. Pellet the cells in a microcentrifuge for 30 seconds. Remove the media supernatant.
8. (Integration step) Resuspend the cells in 1 ml LB+Chloramphenicol (25 μg/ml)+Kanamycin (50 μg/ml)+Glucose (0.2%) and grow overnight at 37° C., shaking.
9. Dilute the overnight culture 1:10,000 in the same media and grow an additional 16-24 hours at 37° C.
10. (Counter selection step) Dilute 10 μl of the culture into 1 ml 1xM9 minimal salts (to minimize growth rate). Split this into two tubes of 0.5 ml each. To one add Arabinose to 0.2% and to the other add Glucose to 0.2% (to serve as a negative control). Grow 1-2 hours at 37° C. with shaking.
11. Plate 10 μl of the Arabinose tube onto LB+Kanamycin (50 μg/ml)+Arabinose (0.2%) and 10 μl of the Glucose tube onto LB+Chloramphenicol (25 μg/ml)+Kanamycin (50 μg/ml)+Glucose (0.2%). Grow overnight at 37° C.
12. (Screen for mutant) Perform step 9 of the primary protocol.

EXAMPLES

The invention is further defined in the following Example(s). It should be understood the Example(s) are given by way of illustration only. From the above discussion and the Example(s), one skilled in the art can ascertain the essential characteristics of the invention, and without departing from the spirit and scope thereof, can make various changes and modifications to adapt the invention to various uses and conditions. As a result, the invention is not limited by the illustrative example(s) set forth hereinbelow, but rather defined by the claims appended hereto.

Example 1

Plasmids

The plasmid used for PCR construction of the artificial inserted DNA sequence was designated pSG76-CS (GenBank Accession No. AF402780), which was derived from pSG76-C (Posfai et al., 1997) by inserting a second I-SceI site. The second I-SceI site was obtained by the PCR-mediated insertion of a second I-SceI recognition site into pSG76-C, downstream of the NotI site. The two I-SceI sites are in opposite direction.

The pBADαβγ plasmid was used for enhancing recombination of linear DNA-fragments into the genome. This plasmid was described in Muyers et al. (1999).

The PKSUC1 plasmid (GenBank Accession No. AF402779), for expressing I-SceI, was derived from pSG76-K (Posfai et al., 1997) and pUC19RP12 (Posfai et al., 1999). The XbaI-NotI fragment (carries the Kan gene; the NotI end was blunted by Klenow polymerase) of pSG76-K was ligated to the XbaI-DraI fragment (carries the I-SceI gene and the pUC ori) of pUC19RP12.

The pKSUC5 plasmid for tetracycline-regulated expression of I-SceI was derived from pFT-K (Posfai et al., 1997) and pKSUC1. The large XbaI-NcoI fragment of pKSUC1 was ligated to the XbaI-NcoI fragment of pFT-K carrying the tet repressor.

The PKD46 plasmid for enhancing recombination of linear DNA-fragments into the genome was described in Datsenko et al. (2000).

The plasmid pSTKST (GenBank Accession No. AF406953) is a low copy number $Kan^R$ plasmid for chlortetracycline-regulated expression of I-SceI, derived from pFT-K (Posfai et al., 1997) and pUC19RP12 (Posfai et al., 1999). The XbaI-PstI fragment from pUC19RP12, carrying the I-SceI gene, was ligated to the large XbaI-PstI fragment of pFT-K. This plasmid expresses I-SceI when induced by chlortetracycline. Replication of the plasmid is temperature-sensitive (Posfai et al., 1997).

The plasmid pSTAST, a low copy number $Ap^R$ plasmid for chlortetracycline-regulated expression of I-SceI, was derived from pFT-A (Posfai et al., 1997) and pUC19RP12 (Posfai et al., 1999). The XbaI-PstI fragment from pUC19RP12, carrying the I-SceI gene, was ligated to the large XbaI-PstI fragment of pFT-A. This plasmid expresses I-SceI when induced by chlortetracycline. Replication of the plasmid is temperature-sensitive (Posfai et al., 1997).

Deletion Procedure 1

This describes the process used to repeatedly make deletions from the genome of E. coli K-12. This procedure is a scarless deletion method. The procedure begins with the construction of a linear target fragment by PCR. This was done by mixing 20 pmol of primer A with 20 pmol primer B, and performing PCR in a total volume of 50 μl. The cycle parameters used were 15×(94° C. 40 sec/57° C. or lower (depending on the overlap of A and B) 40 sec/72° C. 15 sec). The 1 μl of the PCR mix above were taken, added to 20 pmol of primers A and C each, add 50 ng of pSG76-CS and perform PCR in a volume of 2×50 μl (use 50-μl tubes, and two tubes are combined to have more DNA). The cycle parameters used were 28×(94° C. 40 sec/57° C. 40 sec/72° C. 80 sec). To purify the PCR mix from the above step, Promega Wizard PCR purification kit was used. The resulting DNA fragment was suspended in 20 μl water.

Next was the replacement of a genomic region by insertion of the artificial DNA-fragment. This was done by taking the target cell carrying pBADαβγ and preparing electrocompetent cells as described (Posfai et al., 1999), except that 0.1% arabinose was added to the culture 0.25-1 hour before harvesting the cells. 4 μl of DNA fragments (100-200 ng) were electroporated into 40 μl of electrocompetent cells. The cells were plated on Cam plates (25 μg cam/ml) and incubated at 37° C. The usual result was to obtain a total of 10 to several hundred colonies after overnight incubation. A few colonies were checked for correct site insertion of the fragment by PCR using primers D and E.

Next was the deletion of the inserted sequences. This was done by preparing competent cells derived from a selected colony from above by the $CaCl_2$ method (Sambrook et al., 1989). The plasmid pKSUC1 (~100 ng) was transformed into the cells by standard procedures (Sambrook et al., 1989). The cells were plated on Kan plates and incubated at 37° C. (pKSUC1 and pBADαβγ are incompatible, thus selection on Kan eliminates pBADαβγ from the cells). The colonies were checked for correct deletion by PCR using primers D and E. A colony was selected carrying the correct deletion. At this point, the cells carried pKSUC1. The next step is to delete this plasmid.

This deletion is done through the replacement of pKSUC1 with pBADαβγ. A colony from the prior step was selected, grown in LB at 37° C. under nonselective conditions, reinoculating the cells into fresh medium 2-3 times. Competent cells were prepared for either chemical transformation or electroporation. The plasmid pBADαβγ (100-200 ng) was transformed into the competent cells which were plated on Amp plates. A colony which was Kan sensitive/Amp resistant was selected by toothpicking a hundred colonies on Kan and Amp plates.

The selected colony can be used in a next round of deletion by using a new targeting fragment and repeating the steps above. If no more deletions are needed, growing the cells under nonselective conditions (no Amp is added) results in the spontaneous loss of pBADαβγ from a large fraction of the cells.

Deletion Procedure 2

This procedure is similar to procedure 1, but pKSUC1 is replaced by pSTKST. This plasmid is compatible with pBADαβγ, has a temperature-sensitive replicon, and expression of I-SceI requires induction by chlortetracycline (CTC). The advantage is that elimination of pSTKST from the cell is easily accomplished by growing the culture at 42° C.

Construction of a linear targeting fragment by PCR and replacement of a genomic region by insertion of the fragment are done as described in Procedure 1.

To delete the inserted sequences competent cells are prepared from a culture derived from a selected colony harboring the right insertion. Cells are transformed by pSTKST, plated on Kan+Cam plates and incubated at 30° C. A colony from this plate is inoculated into 10 ml of LB+Kan supplemented with heat-treated inducer CTC (25 μg/ml final concentration) and grown at 30° C. for 24 hours. This step serves induction of the expression of I-SceI. Dilutions of the culture are then spread on LB+Kan plates and incubated overnight at 30° C. 6-12 colonies were checked for correct deletion by PCR using primers D and E. A colony was selected carrying the correct deletion.

To eliminate the helper plasmids from the cell, the culture is grown at 42° C. in LB (no antibiotics added).

Procedure 3

Since pBADαβγ and pSTKST carry compatible replicons, repeated transformations of the plasmids are not required when consecutive deletions are made in the same host. The two plasmids are maintained in the host cell throughout consecutive deletion constructions by antibiotic selection (Kan+Amp). Recombinase and specific nuclease functions are induced only when needed. Since replication of pSTKST is temperature-sensitive, cells must be grown at 30° C.

The procedure is identical to Procedure 2, except that pBADαβγ and pSTKST are transformed into the cell only once, and until maintenance of both plasmids in the cell is desired, the culture is grown at 30° C., and Amp+Kan are included in the medium. Note: Sometimes the inventors experienced difficulties in growing the cells at 30° C. in the presence of two (Amp+Kan) or three (Amp+Kan+Cam) antibiotics.

Procedure 4

This is the particular procedure when several consecutive deletions are to be made in the same cell. Insertions (recombination of linear fragments into the genome of a host cell carrying pBADαβγ) are made in parallel, creating a series of recombinant cells, each carrying a single insertion. These insertions are then transferred one by one by P1 transduction into the cell carrying pSTKST and harboring all previous deletions. Removal of all foreign sequences is done in this final host by inducing pSTKST. Compared to the previous methods, the main difference is that the insertion step and removal of the inserted sequences are done in separate cells. Since insertions are made in parallel, the construction of consecutive deletions is faster. Another advantage is that cells are transformed by the plasmids only at the beginning of the first deletion construction.

Technically the procedure is identical to Procedure 2, except that individual insertions are transferred by P1 transduction to the deletion strain already harboring pSTKST. After each P1 transduction step, I-SceI expression is induced to remove the inserted sequences.

Results

Twelve consecutive genomic deletions have been made from *E. coli* strain K-12 MG1655. The twelve deleted regions were selected for deletion, in part, as a result of comparison of the genomic DNA sequences of *E. coli* strain O157:H7 EDL933 and strain K-12 MG1655. The deletions are listed on Table 1 below. The sequence numbering is taken from the published K-12 sequence.

The first deletion MD1 was made using the method described in Posfai et al. (1999). Using this method for creating MD1 deletion left a 114-bp pSG76-CS vector sequence, including a FRT site, in the chromosome at the site of deletion. MD2 through MD6 deletions were made using Procedure 1 described above. Deletions MD7 through MD12 were created using a combination of Procedure 4 and Procedure 1 or 2. Strain designations and genomic coordinates of each new deletion were: MD1 263080-324632; MD2 1398351-1480278; MD3 2556711-2563500; MD4 2754180-278970; MD5 2064327-2078613; MD6 3451565-3467490; MD7 2464565-2474198; MD8 1625542-1650865; MD9 4494243-4547279; MD10 3108697-3134392; MD11 1196360-1222299; MD12 564278-585331.

A total of 378,180 base pairs, which is approximately 8.1% of the native K-12 MG1655 *E. coli* genome, was removed at this stage. Removing these regions from the genome did not affect bacterial survival or bacterial growth.

Table 2 below lists other segments, genes and regions of the *E. coli* genome that were identified as candidates for further deletions. The segments were also successfully removed from the genome of the bacteria. Again, these deletions were made without any apparent deleterious effect on the usefulness of the bacteria for laboratory and industrial use. Again the sequence designations are taken from the published K-12 sequence. The two sets of deletions totaled about 14% of the original bacterial genome. It should be noted that it is possible to delete the genes themselves along with flanking DNA so long as the flanking DNA does not disrupt a gene essential for growth and survival of the host.

In Procedure 1, efficiency of the insertion of the linear fragment varied with the particular genomic locus. Correct-site insertion occurred in 1-100% (normally 20-100%) of the colonies. Flanking homologies in the range of 42 to 74 bp were used. Longer homologies give better insertion efficiencies. Correct-site excision between the duplicated sequences occurred in 1-100% (normally 10-100%) of the colonies and depended on the length of the duplicated region. Longer duplications are usually more effective. Length of the duplicated sequences was in the range of 42 to 50 bp. Variations in the efficiencies of insertion and excision existed between seemingly identically repeated experiments and are not fully understood yet.

Procedure 3 was tested by re-creating deletion MD2. Correct-site insertion of the linear DNA-fragment occurred in 6.6% of the colonies. Deletion of the inserted sequence was very efficient. Twenty-five resulting colonies were replica plated on Cam+Amp+Kan and Amp+Kan plates, and 19 of them proved to be Cam sensitive. Five of these colonies were then tested by PCR, and all 5 showed the predicted loss of the inserted sequence.

Table 8 and Table 9 show a more precise description of the deletion endpoints of genes that have been or will be deleted from the landmark. *E. coli* strains MDS12, MDS40 and MDS73 (Tables 8 and 9) are the endpoints of the deletions for intermediate strains that were used to construct the landmark strains. The genes listed in Table 9 identified by "b" numbers and are based on the designations set out in Blattner et al., *Science*, supra and in GenBank Accession No. 400096. The numbering in Table 8 is also based on Blattner et al. supra.

Characterization of Deletion Strains

Transformation Frequency

It is desirable to incorporate exogenous DNA into the genome of *E. coli* deleted strains in such a way that host bacterial cells will maintain the integrated DNA as they divide and grow. The process of exogenous DNA introduction into bacterial host genome is called transformation and organisms who harbor exogenous DNA are called transformed organisms. There is need in the art for *E. coli* strains with high efficiency of transformation.

*E. coli* strain MDS39 was constructed by making 39 deletions (approximately 14.1% of the genome) in parental *E. coli* strain MG1655 and was found to be efficiently transformed by electroporation. This high efficiency of transformation extended to intake of a large size BAC (Bacterial Artificial Chromosome) DNA, which makes the strain MDS39 particularly valuable for the wide range of applications.

To test the transformation efficiency of *E. coli* strain MDS39 in harboring and stably maintaining exogenous DNA, three strains: DH10B, MDS31 and MDS39 were grown under standard growth conditions to optical density of 0.5 at 600 nm. Cell cultures were spun down, cell pellets were washed several times with water and finally resuspended in water (at 1/1000 of the original culture volume). 25 ng of either pBR322DNA or methylated BAC DNA or unmethylated BAC DNA was added to 100 µl of the cell suspension and subjected to electroporation using standard electroporation protocol, e.g., 1.8 kV and resistance of 150 ohms in a 0.1 cm electroporation cuvette using an Invitrogen Electroporator II™ device. BAC DNA methylated at the EcoK sites and pBR322DNA were prepared in *E. coli* strain MG1655 using standard protocols. Unmethylated BAC DNA was prepared in *E. coli* strain DH10B.

Table 3 shows that both strains, MDS31 and MDS39, are efficiently transformed by pBR322DNA with molecular weight of 4,363 base pairs and by methylated BAC DNA with molecular weight of 100,000 base pairs. The efficiencies of transformation with methylated BAC DNA for strains MDS31 and MDS39 are comparable with the efficiency of transformation for strain DH10B which is currently regarded as one of the strains with the best transformation efficiency.

When transformed with unmethylated BAC DNA, the efficiency of transformation for strain MDS39 was higher than the efficiency of transformation for strain DH10B (Table 3), while the efficiency of transformation for strain MDS31 was lower then the efficiencies of transformation for both strains MDS39 and DH10B. The low efficiency of transformation for strain MDS31 is due to the fact that the unmethylated DNA is a subject to restriction in the strain because MDS31 is a $r^+m^+$ strain, while both strains DH10B and MDS39 are $r^-m^-$ strains.

Recent work with MDS39 revealed the possible presence of a residual insertion sequence IS5 in sequence gb_ba:ecu 95365. In order to determine the effect of deleting of deleting the resident IS sequence from MDS39, procedures described herein were used to delete the sequence. The endpoints of the deletions in MDS40 are strains in Tables 8 and 9. The resulting strain MDS40 was then tested for its transformation offering and growth characteristics (Results) as discussed below.

Electroporation-competent cells were prepared as described in the Invitrogen Electroporator II Manual. Briefly, a 200-ml culture was grown to $OD_{550}$=0.5, then cells were harvested by centrifugation and washed twice in ice-cold water and once in ice-cold 10% glycerol by repeated centrifugation and suspension. At the final step the cell pellet was suspended in 0.4 ml 10% glycerol, aliquoted in 40 µl portions and stored at −80° C.

The cells were typically electroporated with 10-100 ng quantities of plasmid DNA at 1.8 kV and a resistance of 150Ω in a 0.1-cm electroporation cuvette using the Electroporator II device (Invitrogen). Cells were then diluted with 1 ml LB, incubated in a shaker for 1 h, and plated on selective medium.

Several experiments were done, results may vary by an order of magnitude. The average of 2 typical, independent experiments (2 parallels each) are shown in Table 5.

Transformation efficiencies for MG1655, MDS40 and DH10B used chemical transformation methods were also used. Competent cells were prepared by a simple method. A 50-ml culture was chilled and harvested by centrifugation at $OD_{550}$=0.4, then washed twice with 1/20 volume of ice-cold $CaCl^2$ solution (10 mM Tris pH 7.5, 15% glycerol, 60 mM $CaCl_2$) with repeated centrifugation and suspension. Cells were then incubated on ice for 1 h, aliquoted in 200-µl portions and stored at −80° C.

For transformation, cells were typically mixed with 100 ng plasmid DNA, incubated on ice for 30 min, heat-shocked at 42° C. for 2 min, then 0.8 ml LB was added. Cells were incubated at 37° C. for 0.5-1 h, then dilutions were plated on selective medium. Results are shown in Table 6.

Growth Characteristics

As discussed above it is desirable that deletion strains prepared by the methods of the present invention have a robust ability to grow under certain culture conditions. Growth studies were conducted as follows.

Comparison of *E. coli* strain cell doubling time in minutes at 37° C. was measured with a 96-well plate reader (SpectraMax plus, Molecular Devices) with shaking. The log linear portion of the growth curve was used to calculate the average doubling times and standard deviation from six replicates on the plate. This device, while providing a convenient way to do comparative measurements does not areate the cells very well so the rates of growth about twice as slow as obtained with shake flasks.

It is evident the deletion strains grow at the same rate in minimal medium as the original MG1655 but not to the same ultimate density. The deletions grow less rapidly but the same ultimate density on rich defined medium. It will be interesting to examine the reasons for these small differences, but the objective of reducing the genome substantially while preserving the ability to grow robustly in minimal medium has clearly been achieved.

Example 2

Stress-Induced Reactivation of Cryptic Prophage

Figure 7:
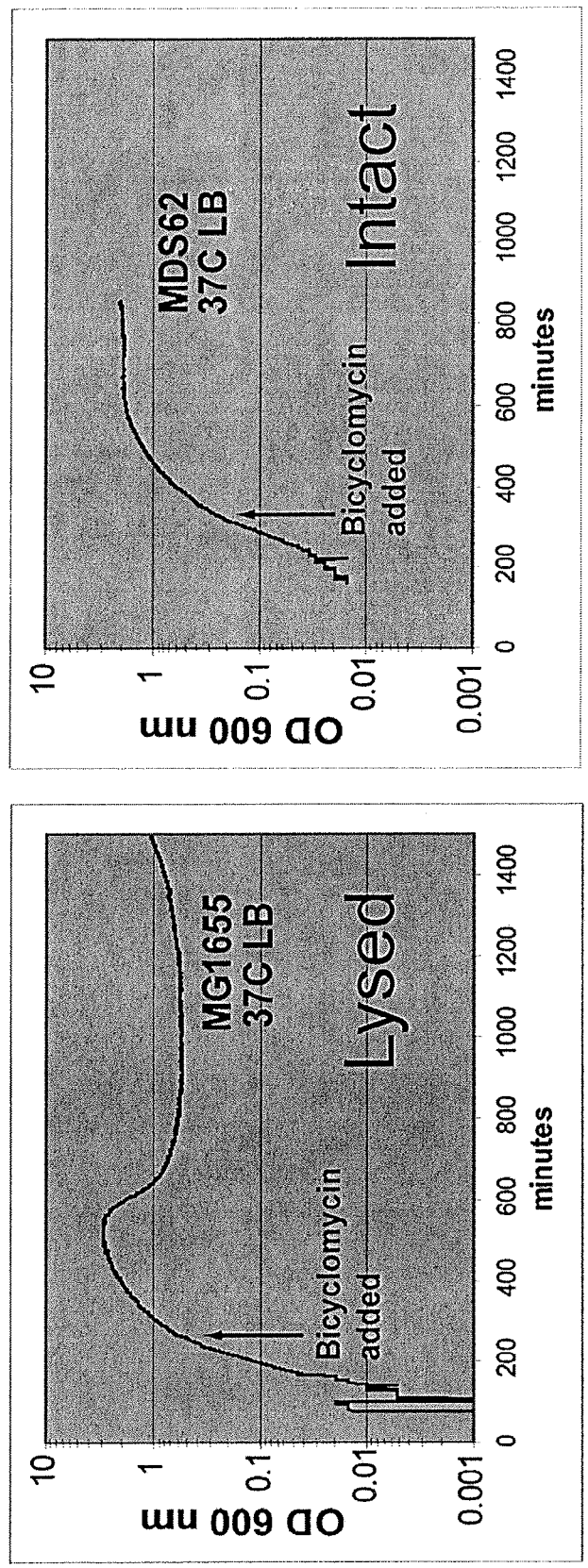
FIG. 7 illustrates the effect of stress-induced prophage reactivation on the growth of MG1655 (native parent strain) and MDS62 (a reduced genome strain lacking all prophage elements).

The effect of stress-induced prophage reactivation on the growth of parent *E. coli* strain MG1655 was tested. Briefly, MG1655 was grown under standard growth conditions to early log phase at which time bicyclomycin (100 µg/ml) was added. The effect of bicyclomycin on growth was then followed. Bicyclomycin is an antibiotic which disrupts the activity of Rho, a transcription termination factor which is essential for viability of gram negative bacteria such as *E. coli*. The *E. coli* genes most repressed by Rho are found within the endogenous prophages; accordingly, bicyclomycin provides a means for testing the effects of derepressing (i.e. activating) prophage elements in *E. coli*. MG1655 continued to grow to an optical density of ~5.0 at 600 nm after which a sharp decline in optical density was observed (FIG. 7, left panel). In a parallel experiment, MDS62, a reduced genome strain comprising a ~20% genome reduction including deletion of all prophage elements (MDS62 deletions are set forth at Tables 1 and 2), was grown under identical conditions and bicyclomycin (100 µg/ml) added at the same optical density after which growth was followed. Strikingly, no decline in optical density was observed following addition of bicyclomycin (FIG. 7, right panel); rather, MDS62 cells exhibited the same growth pattern observed in the absence of bicyclomycin. Thus, deletion of prophage elements confers resistance to bicyclomycin.

Figure 8:
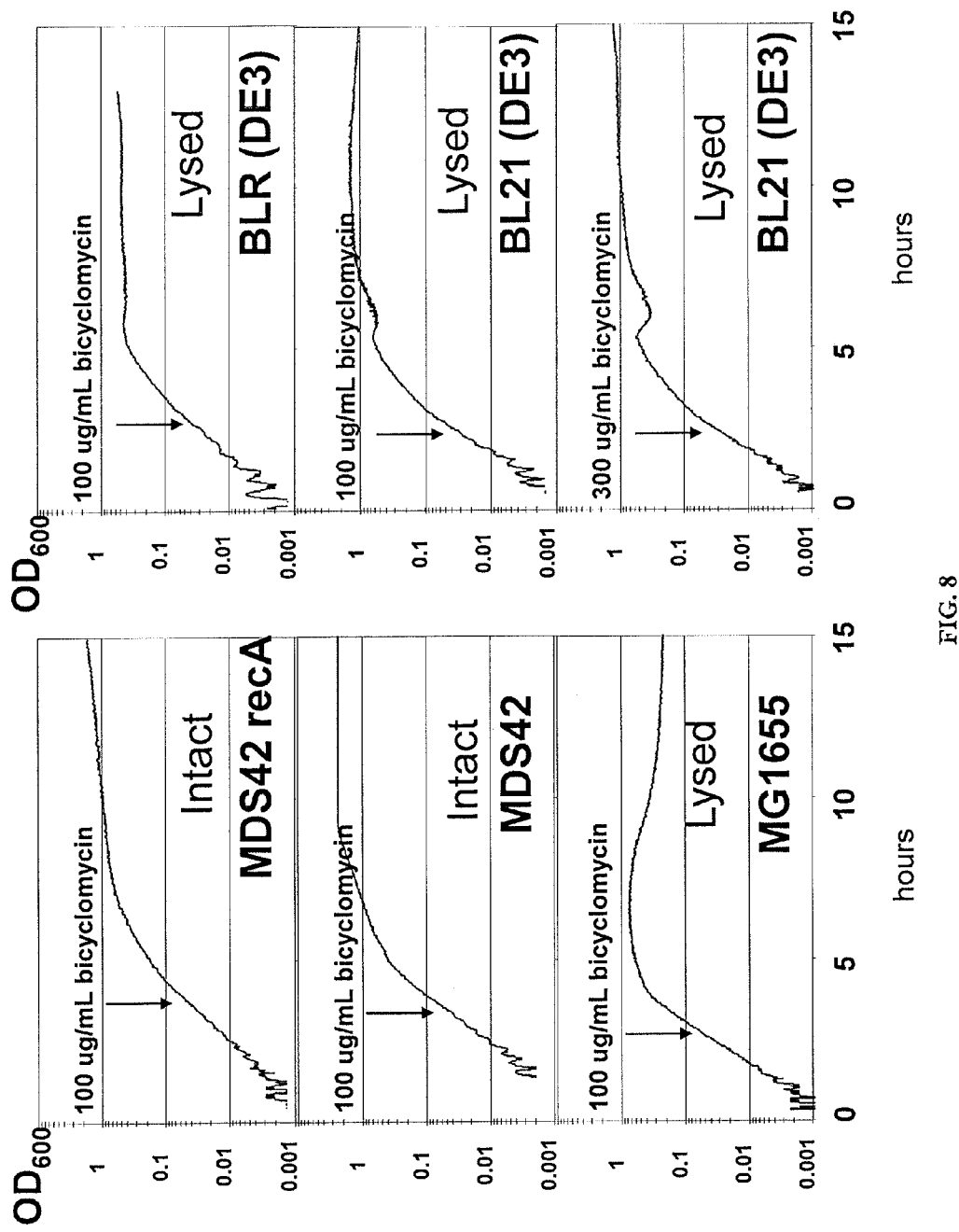
FIG. 8 illustrates microscopic visualization of the effect of stress-induced prophage reactivation on the growth of MG1655, MDS42recA, MDS42, BLR(DE3) and BL21 (DE3).
Figure 9:
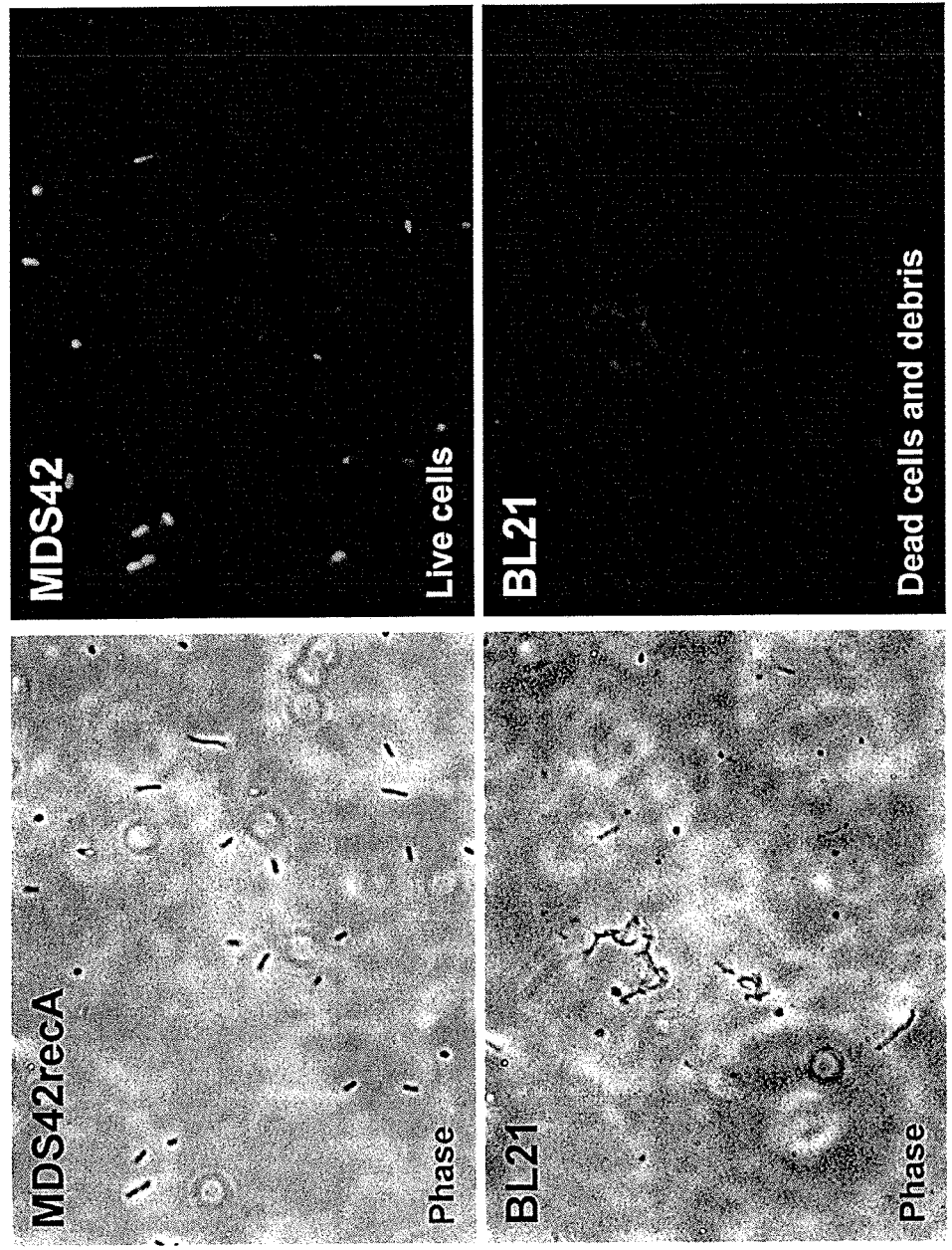
FIG. 9 illustrates the effect of bicyclomycin on viability of MDS42 and BL21(DE3).

The effect of bicyclomycin on growth (standard conditions) of reduced genome strains MDS42 and MDS42recA was also tested and compared to parent strain MG1655. These strains, which also lack all prophage elements also exhibited resistance to bicyclomycin (FIG. 8, left panel); growth was identical to that observed in the absence of bicyclomycin.

Next, the effects of bicyclomycin on growth of an *E. coli* B strain, BL21(DE3), was tested. BL21(DE3) exhibited a sharp decline in optical density following addition of bicylomycin, similar to that observed for MG1655, confirming that both B and K12 strains are sensitive to reactivation of prophage elements.

Morphology of bicyclomycin-induced cultures was then examined. Briefly, samples of MDS42 and BL21 bacteria were collected following addition of bicyclomycin and stained for visualization. Microscopy confirmed that addition of bicyclomycin causes BL21 bacteria to lyse whereas MDS42 bacteria are resistant. Thus, deletion of prophage elements confers resistance of gram negative bacteria such as *E. coli* to bicyclomycin. Reactivation of prophage elements in native parent *E. coli* strains, as exemplified by MG1655 and BL21, causes the cells to lyse, presumably because the gene products of these prophage elements are toxic to the cell. In this respect, lysozyme, a product of prophage elements, destroys the cell wall of certain bacteria (e.g., *E. coli*) and likely contributes to the observed lysis of MG1655 and BL21 cells following addition of bicyclomycin.

Figure 10:
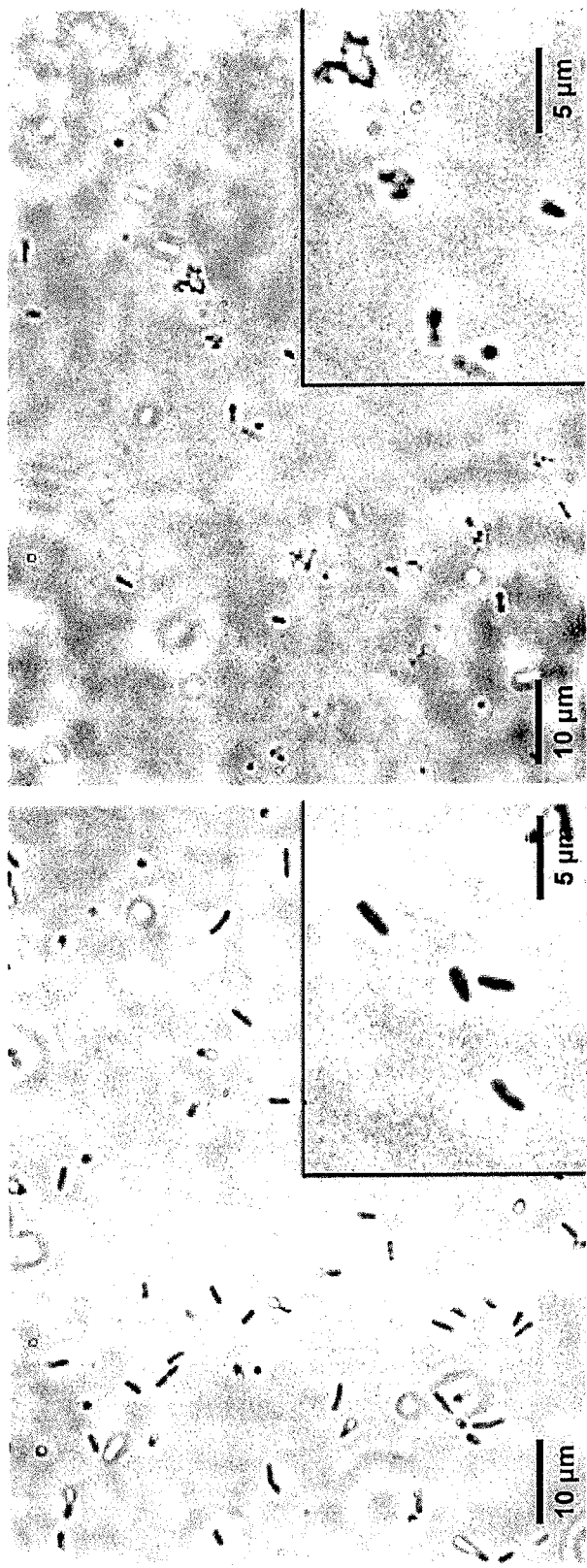
FIG. 10 illustrates the effect of overexpressing gelsolin (a heterologous protein) on viability of MDS42 (left panel) and BL21(DE3) (right panel). MDS42 remains viable even when expressing gelsolin at concentrations greater than 25 g/L whereas BL21 cells lyse when expressing gelsolin at 1.3 g/L.

Expression of gene products at high concentrations, even products whose expression is tolerated at lower concentrations, can activate the stress response in bacteria thereby limiting their usefulness as host cells for the production of biological reagents. The effect of deleting prophage elements on expression of a heterologous protein was tested. MDS42 and BL21 bacteria were transformed with an expression vector for human plasma gelsolin, then grown to high cell densities in fed-batch fermentations on minimal medium. Expression of the heterologous protein product was induced by addition of IPTG. MDS42 bacteria remained viable even when expressing gelsolin at concentrations above 25 g/L (FIG. 10, left panel). BL21 bacteria, on the other hand, lysed even when expressing gelsolin at a concentration of 1.3 g/L (FIG. 10, right panel). Thus, removal of prophage elements was demonstrated to eliminate stress-induced cell lysis thereby enabling a nearly 20-fold increase in production of the heterologous protein. Bacterial strains lacking prophage elements are surprisingly advantageous hosts for production of gene products.

Reduced Genome *E. coli* B Strains

Table 10 shows a precise description of the deletion endpoints of genes that have been or will be deleted from *E. coli* strain BL21(DE3). The right and left sequence of the primers used to make the deletions are listed at Table 11. Seven consecutive genomic deletions have been made thus far, the first of which resulted in strain BL1, the second of which resulted in strain BL2 and so on up to strain BL7. Among the genomic regions deleted to date are all DLP12 and CP4-44 prophage elements. Future BL21(DE3)-derived strains will have all DLP12, λ*B, RybB*B, Rac, Qin, CP-44, SsrA*B, PheV*B, SelC*B and KpLE2 prophage elements deleted therefrom and all insertion sequences deleted therefrom using the methods described herein. DE3, a λ prophage carrying the T7 polymerase gene which renders this strain suitable for production of protein from target genes cloned in T7-driven expression vectors, is not among the planned deletions. The sequence numbering is taken from the published BL21(DE3) sequence (GenBank Accession No. CP001509).

The deletions were made using the Procedures described above. The genomic coordinates of the planned and carried out deletions are: BMD1 15385-24623; BMD2 241256-243669; BMD3 262791-264601; BMD4 352423-357555; BMD5 376748-377531; BMD6 536916-592056; BMD7 619107-638679; BMD8 658152-671312; BMD9 1193606-1194384; BMD10 1322339-1325012; BMD11 1398349-1451586; BMD12 1460130-1460927; BMD13 1857061-1858411; BMD14 1973270-1974687; BMD15 2004159-2011036; BMD16 2031433-2072701; BMD17 2128600-2129378; BMD18 2139556-2143995; BMD19 2262740-2263509; BMD20 2406676-2408561; BMD21 2616656-2618847; BMD22 2677319-2685932; BMD23 2772836-2775877; BMD24 2821970-2834720; BMD25 2996251-3070465; BMD26 3433461-3434239; BMD27 3651091-3662535; BMD28 3736504-3742367; BMD29 3893549-3894996; BMD30 4479765-4586245.

A total of 440,337 base pairs, which is approximately 9.5% of the native BL21(DE3) *E. coli* genome, will be removed, including all prophage elements and all insertions sequences. To date, approximately 145,344 base pairs, which is approximately 3.1% of the native BL21(D3) *E. coli* genome has been removed, including all DLP12 and CP4-44 prophage elements, with no significant effect on bacterial survival or bacterial growth.

TABLE 1

FIRST COMPLETED DELETIONS

| Deletion | Endpoints[a] | Size (bp) | Description[b] |
|---|---|---|---|
| MD1 | 263080, 324632 | 61553 | b0246-b0310; includes K-islands #16, 17, 18, CP4-6, eaeH |
| MD2 | 1398351, 1480278 | 81928 | b1336-b1411; includes K-island #83, Rac |
| MD3 | 2556711, 2563500 | 6790 | b2441-b2450; includes K-island #128, CP-Eut |
| MD4 | 2754180, 2789270 | 35091 | b2622-b2660; includes K-island #137, CP4-57, ileY |
| MD5 | 2064327, 2078613 | 14287 | b1994-b2008; includes K-islands #94, 95, 96, CP4-44 |
| MD6 | 3451565, 3467490 | 15926 | b3323-b3338; includes K-islands #164, 165 |

TABLE 1-continued

FIRST COMPLETED DELETIONS

| Deletion | Endpoints[a] | Size (bp) | Description[b] |
|---|---|---|---|
| MD7 | 2464565, 2474198 | 9634 | b2349-b2363; includes K-island #121 |
| MD8 | 1625542, 1650785 | 25244 | b1539-b1579; includes K-island #77, Qin |
| MD9 | 4494243, 4547279 | 53037 | b4271-b4320; includes K-island #225, fec operon, fim operon |
| MD10 | 3108697, 3134392 | 25696 | b2968-b2987; includes K-island #153, glc operon |
| MD11 | 1196360, 1222299 | 25940 | b1137-b1172; includes K-island #71, e14 |
| MD12 | 564278, 585331 | 21054 | b0538-b0565; includes K-island #37, DLP12 |

TABLE 2

SECOND SET OF COMPLETED DELETIONS

IS186 deletions (3)

| | |
|---|---|
| keep dnaJ | 14168, 15298 (+) |
| *delete GP1 | 15388, 20563 IS186, gef, nhaAR, IS1 |
| [IS186 | 15388, 16730] |
| [IS1 | 19796, 20563] |
| keep rpsT | 20815, 21078 (−) |
| keep pheP | 601182, 602558 (+) |
| *delete GP2 | 602639, 608573 ybdG, nfnB, ubdF, ybdJ, ybdK, IS186 |
| {IS186 | 607231, 608573] |
| keep entD | 608682, 609311 (−) |
| keep glk | 2506481, 2507446 (−) |
| *delete GP3 | 2507650, 2515969 b2389, b2390, b2391, b2392, nupC, IS186, yfeA |
| [IS186 | 2512294, 2513636] |
| keep alaX | 2516061, 2516136 (−) |

IS2 deletions (3 not already deleted)

| | |
|---|---|
| Keep yaiN | 378830, 379126 (−) |
| *delete GP4 | 379293, 387870 yaiO, b0359, IS2, b0362, yaiP, yaiS, tauABCD |
| [IS2 | 380484, 381814] |
| keep hemB | 387977, 388984 (−) |
| *delete GP5 | 389121, 399029 b0370, yaiT, IS3, yaiU, yaiV, ampH, sbmA, yaiw, yaiY, yaiZ |
| [IS3 | 390933, 392190] |
| keep ddlA | 399053, 400147 (−) |
| keep ygeK | 2992482, 2992928 (−) |
| *delete GP6 | 2992959, 2996892 b2856, b2857, b2858, b2859, IS2, b2862, b2863 |
| [IS2 | 2994383, 2995713] |
| keep glyU | 2997006, 2997079 (−) |
| keep ribB | 3181829, 3182482 (−) |
| *delete GP7 | 3182796, 3189712 b3042, ygiL, IS2, yqiGHI (fimbral locus) |
| [IS2 | 3184112, 3185442] |
| keep glgS | 3189755, 3189955 (−) |

IS5 deletions (6 not already deleted)

| | |
|---|---|
| keep ybeJ | 686062, 686970 (−) |
| *delete GP8 | 687074, 688268 IS5 |
| keep Int | 688566, 690104 (−) |
| keep tpx | 1386329, 1386835 (−) |
| *delete GP9 | 1386912, 1396646 ycjG, ycjI, ycjY, ycgZ, mppA, ynaI, IS5, ynaJ, ydaA |
| [IS5 | 1394068, 1395262] |
| keep fnr | 1396798, 1397550 (−) |
| keep gnd | 2097884, 2099290 (−) |
| *delete GP10 | 2099418, 2135739 IS5 plus entire O Antigen and Colanic Acid clusters |
| [IS5 | 2099771, 2100965] |
| keep yegH | 2135858, 2137507 (+) |
| keep proL | 2284231, 2284307 (+) |
| *delete GP11 | 2284410, 2288200 yejO and IS5 |
| [IS5 | 2286939, 2288133] |
| keep narP | 2288520, 2289167 (+) |
| keep gltF | 3358811, 3359575 (+) |
| *delete GP12 | 3359747, 3365277 IS5 plus yhcADEF (K-island) |
| [IS5 | 3363191, 3364385] |
| keep yhcG | 3365462, 3366589 (+) |
| keep arsC | 3647867, 3648292 (+) |
| *delete GP13 | 3648921, 3651343 yhis and IS5 |

TABLE 2-continued

SECOND SET OF COMPLETED DELETIONS

| | |
|---|---|
| (IS5 | 3640666, 3650860] |
| keep slp | 3651558, 3652157 (+) |
| flagella | |
| Region I | |
| keep mviN | 1127062, 1128597 (+) |
| *delete GP14 | 1128637, 1140209 flgAMN flgBCDEFGHIJKL |
| keep rne | 1140405, 1143590 (−) |
| Region II | |
| keep yecT | 1959975, 1960484 (+) |
| *delete GP15 | 1960605, 1977294 flh, che, mot, tap, tar, IS1 |
| keep yecG | 1977777, 1978205 (+) |
| Regions IIIa and IIIb try deleting both in one action | |
| keep sdiA | 1994133, 1994855 (−) |
| *delete Gp16 | 1995085, 2021700 fli, plus amyA, yec and yed ORFS |
| keep rcsA | 2021990, 2022613 (+) |
| hsd region | |
| keep uxuR | 4552145, 4552918 (+) |
| *delete GP17 | 4553059, 4594581 yji ORFS, plus mcrBCD, hsdRMS, mrr, tsr |
| keep mdoB | 4594719, 4596971 (−) |
| Rhs elements | |
| keep ybbP | 519640, 522054 (+) |
| *delete GP18 | 522062, 529348 RhsD element & associated ORFs |
| keep ybbB | 529356, 530450 (−) |
| keep ybfA | 728357, 728563 (+) |
| *delete GP19 | 728616, 738185 RhsC element & associated ORFs |
| keep ybgA | 738224, 738733 (+) |
| keep yncH | 1524964, 1525176 (+) |
| *delete GP20 | 1525914, 1531648 RhsE element & associated ORFs |
| keep nhoA | 1532048, 1532893 (+) |
| keep nikR | 3616219, 361662 (+) |
| *delete GP21 | 3616623, 3623309 RhsB element & associated ORFs # may need to leave something here to separate converging ORFs? |
| keep yhhJ | 3623310, 3624437 (−) |
| keep yibF | 3758974, 3759582 (−) |
| *delete GP22 | 3759620, 3767868 RhsA element & associated ORFs |
| keep yibH | 3767870, 3769006 (−) |
| the rest of the IS elements | |
| keep appA | 1039840, 1041138 (+) |
| *delete GP23 | 1041253, 1049768 yccZYC (EPS), ymcDCBA (EPS?), IS1 |
| [IS1 | 1049001, 1049768] |
| keep cspH | 1050186, 1050398 (−) |
| keep phoH | 1084215, 1085279 (+) |
| *delete GP24 | 1085329, 1096603 ycdSRQPT (hms homologues), IS3, ymdE, ycdU |
| [IS3 | 1093468, 1094725] |
| keep serX | 1096788, 1096875 (−) |
| keep baeR | 2162298, 216302 (+) |
| *delete GP25 | 2163172, 2175230 P2 remnant, IS3, gat operon |
| [IS3 | 2168193, 2169450] |
| keep fbaB | 2175532, 2176656 (−) |
| keep yhhX | 3577399, 3578436 (−) |
| *delete GP26 | 3578769, 3582674 yhhYZ, IS1, yrhAB |
| [IS1 | 3581059, 3581826] |
| keep ggt | 3582712, 3584454 (−) |
| keep cspA | 3717678, 3717890 (+) |
| *delete GP27 | 3718262, 3719704 IS150 |
| [IS150 | 3718262, 3719704] |
| keep glyS | 3719957, 3722026 (−) |

TABLE 3

Transformation Efficiencies for E. coli Strains MDS31, MDS39 and DH10B

|  | DH10B (transformants per microgram DNA) | MDS31 (transformants per microgram DNA) | MDS39 (transformants per microgram DNA) |
|---|---|---|---|
| pBR322 | $2 \times 10^8$ | $2.2 \times 10^8$ | $2.7 \times 10^8$ |
| Methylated BAC | $2 \times 10^6$ | $0.6 \times 10^6$ | $1.2 \times 10^6$ |
| Unmethylated BAC | $1.8 \times 10^6$ | $4.0 \times 10^3$ | $3.0 \times 10^6$ |

TABLE 4

Deleted Periplasmic Protein Genes

| Deletion | Gene, MR b# | MR Gene | MR Gene Product |
|---|---|---|---|
| GP16 | b1920 | fliY | cysteine transport protein (ABC superfamily, peri_bind) |
| GP16 | b1919 | yedO | D-cysteine desulfhydrase, PLP-dependent |
| GP2 | b0578 | nfnB | dihydropteridine reductase, o2-sensitive NAD(P)H reductase |
| GP4 | b0365 | tauA | taurine transport protein (ABC superfamily, peri_bind) |
| GP9 | b1329 | mppA | periplasmic murein tripeptide transport protein; negative regulator of antibacterial resistance |
| MD2 | b1386 | tynA | copper amine oxidase (tyramine oxidase) |
| MD6 | b3338 | chiA | endochitinase, periplasmic |
| MD9 | b4316 | fimC | periplasmic chaperone required for type 1 fimbrae |
| MD9 | b4290 | fecB | KpLE2 phage-like element; citrate dependent Fe(III) transport protein (ABC superfamily, peri_bind) |
| GP7 | b3047 | yqiH | putative periplasmic chaperone |
| MD1 | b0282 | yagP | putative periplasmic regulator |
| GP12 | b3215 | yhcA | putative periplasmic chaperone |

TABLE 5

Transformation Efficiencies for E. coli Strains MG1655, MDS40 and DH10B

|  | DH10B (transformants per microgram) | MG1655 (transformants per microgram) | MDS40 (transformants per microgram) |
|---|---|---|---|
| pUC19 | $1.3 \times 10^8$ | $2.9 \times 10^8$ | $1.3 \times 10^8$ |
| BAC | $8.8 \times 10^6$ | $3 \times 10^6$ | $6.5 \times 10^6$ |

TABLE 6

Transformation Efficiencies for E. coli Strains MG1655, MDS40 and DH10B

|  | DH10B (transformants per microgram) | MG1655 (transformants per microgram) | MDS40 (transformants per microgram) |
|---|---|---|---|
| pUC19 | $4.5 \times 10^5$ | $3.7 \times 10^4$ | $1.6 \times 10^4$ |

TABLE 7

| Media | Strain | Average Doubling time | Std dev | Max OD |
|---|---|---|---|---|
| MOPS Minimal | MG1655 | 120.41 | 0.63 | 0.82 |
| MOPS Minimal | MDS12 | 123.43 | 6.91 | 0.61 |
| MOPS Minimal | MDS39 | 129.57 | 2.30 | 0.62 |
| MOPS Minimal | MDS40 | 128.26 | 5.30 | 0.61 |
| MOPS Minimal | DH10B | No growth | | |
| Rich Defined | MG1655 | 38.38 | 0.25 | 0.83 |
| Rich Defined | MDS12 | 49.05 | 4.05 | 0.84 |
| Rich Defined | MDS39 | 54.38 | 1.05 | 0.85 |
| Rich Defined | MDS40 | 51.19 | 1.77 | 0.86 |
| Rich Defined | DH10B | 45.40 | 2.30 | 0.62 |

TABLE 8

| MDS12 | MDS40 | MDS73 | del | lend | rend |
|---|---|---|---|---|---|
| deleted | deleted | deleted | MD1 | 263080 | 324632 |
| deleted | deleted | deleted | MD2 | 1398351 | 1480278 |
| deleted | deleted | deleted | MD3 | 2556711 | 2563500 |
| deleted | deleted | deleted | MD4 | 2754180 | 2789270 |
| deleted | deleted | deleted | MD5 | 2064327 | 2078613 |
| deleted | deleted | deleted | MD6 | 3451565 | 3467490 |
| deleted | deleted | deleted | MD7 | 2464565 | 2474198 |
| deleted | deleted | deleted | MD8 | 1625542 | 1650785 |
| deleted | deleted | deleted | MD9 | 4494243 | 4547279 |
| deleted | deleted | deleted | MD10 | 3108697 | 3134326 |
| deleted | deleted | deleted | MD11 | 1196360 | 1222299 |
| deleted | deleted | deleted | MD12 | 564278 | 585331 |
|  | deleted | deleted | GP1 | 15388 | 20562 |
|  | deleted | deleted | GP2 | 602688 | 608572 |
|  | deleted | deleted | GP3 | 2507651 | 2515959 |
|  | deleted | deleted | GP4 | 379334 | 387870 |
|  | deleted | deleted | GP5 | 389122 | 399029 |
|  | deleted | deleted | GP6 | 2993014 | 2996890 |
|  | deleted | deleted | GP7 | 3182797 | 3189712 |
|  | deleted | deleted | GP8 | 687083 | 688267 |
|  | deleted | deleted | GP9 | 1386912 | 1396645 |
|  | deleted | deleted | GP10 | 2099418 | 2135738 |
|  | deleted | deleted | GP11 | 2284421 | 2288200 |
|  | deleted | deleted | GP12 | 3359797 | 3365277 |
|  | deleted | deleted | GP13 | 3648921 | 3651342 |
|  | deleted | deleted | GP14 | 1128620 | 1140209 |
|  | deleted | deleted | GP15 | 1960590 | 1977353 |
|  | deleted | deleted | GP16 | 1995135 | 2021700 |
|  | deleted | deleted | GP17 | 4553059 | 4594581 |
|  | deleted | deleted | GP18 | 522062 | 529349 |
|  | deleted | deleted | GP19 | 728588 | 738185 |
|  | deleted | deleted | GP20 | 1525916 | 1531650 |
|  | deleted | deleted | GP21 | 3616623 | 3623310 |
|  | deleted | deleted | GP22 | 3759620 | 3767869 |
|  | deleted | deleted | GP23 | 1041254 | 1049768 |
|  | deleted | deleted | GP24 | 1085330 | 1096545 |
|  | deleted | deleted | GP25 | 2163173 | 2175230 |
|  | deleted | deleted | GP26 | 3578769 | 3582673 |
|  | deleted | deleted | GP27 | 3718263 | 3719704 |
|  | deleted | deleted | MD40 | 167484 | 173447 |
|  |  | deleted | GP28 | 331595 | 376535 |
|  |  | deleted | GP29 | 1588878 | 1599265 |
|  |  | deleted | GP30 | 3794575 | 3805725 |
|  |  | deleted | GP31 | 3886064 | 3904195 |
|  |  | deleted | GP32 | 2599182 | 2612802 |
|  |  | deleted | GP33 | 3738738 | 3752058 |
|  |  | deleted | GP34 | 4055987 | 4073034 |
|  |  | deleted | GP35 | 1349431 | 1364839 |
|  |  | deleted | GP36 | 2876592 | 2885242 |
|  |  | deleted | GP37 | 149715 | 156883 |
|  |  | deleted | GP38 | 674793 | 682616 |
|  |  | deleted | GP39 | 997082 | 1003880 |
|  |  | deleted | GP40 | 2318063 | 2334712 |
|  |  | deleted | gp41 | 3503000 | 3510000 |
|  |  | deleted | gp42 | 4304000 | 4311000 |
|  |  | deleted | gp43 | 557000 | 563000 |
|  |  | deleted | gp44 | 764000 | 770000 |
|  |  | deleted | gp45 | 1555000 | 1561000 |
|  |  | deleted | gp46 | 2382000 | 2388000 |
|  |  | deleted | gp47 | 2447000 | 2453000 |

TABLE 8-continued

| MDS12 | MDS40 | MDS73 | del | lend | rend |
|---|---|---|---|---|---|
| | | deleted | gp48 | 4547600 | 4553000 |
| | | deleted | gp50 | 747000 | 752000 |
| | | deleted | gp51 | 1727000 | 1732000 |
| | | deleted | gp52 | 2859000 | 2864000 |
| | | deleted | gp53 | 4488000 | 4493000 |
| | | deleted | gp54 | 2520000 | 2524000 |
| | | deleted | gp55 | 4086000 | 4090000 |
| | | deleted | gp56 | 1250000 | 1253000 |
| | | deleted | gp57 | 1650000 | 1653000 |
| | | deleted | gp58 | 2186000 | 2189000 |
| | | deleted | gp59 | 2474000 | 2477000 |
| | | deleted | gp60 | 3358000 | 3360000 |
| | | deleted | gp61 | 3864000 | 3866000 |

TABLE 9

Genes (identified by b-number) deleted for each deletion strain

| | |
|---|---|
| MD1: | b0247, b0248, b0249, b0250, b0251, b0252, b0253, b0254, b0255, b0256, b0257, b0258, b0259, b0260, b0261, b0262, b0263, b0264, b0265, b0266, b0267, b0268, b0269, b0270, b0271, b0272, b0273, b0274, b0275, b0276, b0277, b0278, b0279, b0280, b0281, b0282, b0283, b0284, b0285, b0286, b0287, b0288, b0289, b0290, b0291, b0292, b0293, b0294, b0295, b0296, b0297, b0298, b0299, b0300, b0301, b0302, b0303, b0304, b0305, b0306, b0307, b0308, b0309, b0310 |
| MD2: | b1337, b1338, b1339, b1340, b1341, b1342, b1343, b1344, b1345, b1346, b1347, b1348, b1349, b1350, b1351, b1352, b1353, b1354, b1355, b1356, b1357, b1358, b1359, b1360, b1361, b1362, b1363, b1364, b1365, b1366, b1367, b1368, b1369, b1370, b1371, b1372, b1373, b1374, b1375, b1376, b1377, b1378, b1379, b1380, b1381, b1382, b1383, b1384, b1385, b1386, b1387, b1388, b1389, b1390, b1391, b1392, b1393, b1394, b1395, b1396, b1397, b1398, b1399, b1400, b1401, b1402, b1403, b1404, b1405, b1406, b1407, b1408, b1409, b1410, b1411 |
| MD3: | b2442, b2443, b2444, b2445, b2446, b2447, b2448, b2449, b2450 |
| MD4: | b2622, b2623, b2624, b2625, b2626, b2627, b2628, b2629, b2630, b2631, b2632, b2633, b2634, b2635, b2636, b2637, b2638, b2639, b2640, b2641, b2642, b2643, b2644, b2645, b2646, b2647, b2648, b2649, b2650, b2651, b2652, b2653, b2654, b2655, b2656, b2657, b2658, b2659, b2660 |
| MD5: | b1994, b1995, b1996, b1997, b1998, b1999, b2000, b2001, b2002, b2003, b2004, b2005, b2006, b2007, b2008 |
| MD6: | b3323, b3324, b3325, b3326, b3327, b3328, b3329, b3330, b3331, b3332, b3333, b3334, b3335, b3336, b3337, b3338 |
| MD7: | b2349, b2350, b2351, b2352, b2353, b2354, b2355, b2356, b2357, b2358, b2359, b2360, b2361, b2362, b2363 |
| MD8: | b1540, b1541, b1542, b1543, b1544, b1545, b1546, b1547, b1548, b1549, b1550, b1551, b1552, b1553, b1554, b1555, b1556, b1557, b1558, b1559, b1560, b1561, b1562, b1563, b1564, b1565, b1566, b1567, b1568, b1569, b1570, b1571, b1572, b1573, b1574, b1575, b1576, b1577, b1578, b1579 |
| MD9: | b4271, b4272, b4273, b4274, b4275, b4276, b4277, b4278, b4279, b4280, b4281, b4282, b4283, b4284, b4285, b4286, b4287, b4288, b4289, b4290, b4291, b4292, b4293, b4294, b4295, b4296, b4297, b4298, b4299, b4300, b4301, b4302, b4303, b4304, b4305, b4306, b4307, b4308, b4309, b4310, b4311, b4312, b4313, b4314, b4315, b4316, b4317, b4318, b4319, b4320 |
| MD10: | b2969, b2970, b2971, b2972, b2973, b2974, b2975, b2976, b2977, b2978, b2979, b2980, b2981, b2982, b2983, b2984, b2985, b2986, b2987 |
| MD11: | b1138, b1139, b1140, b1141, b1142, b1143, b1144, b1145, b1146, b1147, b1148, b1149, b1150, b1151, b1152, b1153, b1154, b1155, b1156, b1157, b1158, b1159, b1160, b1161, b1162, b1163, b1164, b1165, b1166, b1167, b1168, b1169, b1170, b1171, b1172 |
| MD12: | b0538, b0539, b0540, b0541, b0542, b0543, b0544, b0545, b0546, b0547, b0548, b0549, b0550, b0551, b0552, b0553, b0554, b0555, b0556, b0557, b0558, b0559, b0560, b0561, b0562, b0563, b0564, b0565 |
| GP1: | b0016, b0017, b0018, b0019, b0020, b0021, b0022 |
| GP2: | b0577, b0578, b0579, b0580, b0581, b0582 |
| GP3: | b2389, b2390, b2391, b2392, b2393, b2394, b2395 |
| GP4: | b0358, b0359, b0360, b0361, b0362, b0363, b0364, b0365, b0366, b0367, b0368 |
| GP5: | b0370, b0371, b0372, b0373, b0374, b0375, b0376, b0377, b0378, b0379, b0380 |
| GP6: | b2856, b2857, b2858, b2859, b2860, b2861, b2862, b2863 |
| GP7: | b3042, b3043, b3044, b3045, b3046, b3047, b3048 |
| GP8: | b0656 |
| GP9: | b1325, b1326, b1327, b1328, b1329, b1330, b1331, b1332, b1333 |
| GP10: | b2030, b2031, b2032, b2033, b2034, b2035, b2036, b2037, b2038, b2039, b2040, b2041, b2042, b2043, b2044, b2045, b2046, b2047, b2048, b2049, b2050, b2051, b2052, b2053, b2054, b2055, b2056, b2057, b2058, b2059, b2060, b2061, b2062 |
| GP11: | b2190, b2191, b2192 |
| GP12: | b3215, b3216, b3217, b3218, b3219 |
| GP13: | b3504, b3505 |
| GP14: | b1070, b1071, b1072, b1073, b1074, b1075, b1076, b1077, b1078, b1079, b1080, b1081, b1082, b1083 |
| GP15: | b1878, b1879, b1880, b1881, b1882, b1883, b1884, b1885, b1886, b1887, b1888, b1889, b1890, b1891, b1892, b1893, b1894 |
| GP16: | b1917, b1918, b1919, b1920, b1921, b1922, b1923, b1924, b1925, b1926, b1927, b1928, b1929, b1930, b1931, b1932, b1933, b1934, b1935, b1936, b1937, b1938, b1939, b1940, b1941, b1942, b1943, b1944, b1945, b1946, b1947, b1948, b1949, b1950 |
| GP17: | b4325, b4326, b4327, b4328, b4329, b4330, b4331, b4332, b4333, b4334, b4335, b4336, b4337, b4338, b4339, b4340, b4341, b4342, b4343, b4344, b4345, b4346, b4347, b4348, b4349, b4350, b4351, b4352, b4353, b4354, b4355, b4356, b4357, b4358 |
| GP18: | b0497, b0498, b0499, b0500, b0501, b0502 |
| GP19: | b0700, b0701, b0702, b0703, b0704, b0705, b0706 |
| GP20: | b1456, b1457, b1458, b1459, b1460, b1461, b1462 |
| GP21: | b3482, b3483, b3484 |
| GP22: | b3593, b3594, b3595, b3596 |
| GP23: | b0981, b0982, b0983, b0984, b0985, b0986, b0987, b0988 |
| GP24: | b1021, b1022, b1023, b1024, b1025, b1026, b1027, b1028, b1029, b1030, b1031 |
| GP25: | b2080, b2081, b2082, b2083, b2084, b2085, b2086, b2087, b2088, b2089, b2090, b2091, b2092, b2093, b2094, b2095, b2096 |
| GP26: | b3441, b3442, b3443, b3444, b3445, b3446 |
| GP27: | b3557, b3558 |
| MD40: | b0150, b0151, b0152, b0153 |
| GP28: | b0315, b0316, b0317, b0318, b0319, b0320, b0321, b0322, b0323, b0324, b0325, |

TABLE 9-continued

Genes (identified by b-number) deleted for each deletion strain

|  |  |
|---|---|
|  | b0326, b0327, b0328, b0329, b0330, b0331, b0333, b0334, b0335, b0336, b0337, b0338, b0339, b0340, b0341, b0342, b0343, b0344, b0345, b0346, b0347, b0348, b0349, b0350, b0351, b0352, b0353, b0354 |
| GP29: | b1507, b1508, b1509, b1510, b1511, b1512 |
| GP30: | b3622, b3623, b3624, b3625, b3626, b3627, b3628, b3629, b3630, b3631, b3632 |
| GP31: | b3707, b3708, b3709, b3710, b3711, b3712, b3713, b3714, b3715, b3716, b3717, b3718, b3719, b3720, b3721, b3722, b3723 |
| GP32: | b2481, b2482, b2483, b2484, b2485, b2486, b2487, b2488, b2489, b2490, b2491, b2492 |
| GP33: | b3573, b3574, b3575, b3576, b3577, b3578, b3579, b3580, b3581, b3582, b3583, b3584, b3585, b3586, b3587 |
| GP34: | b3871, b3872, b3873, b3874, b3875, b3876, b3877, b3878, b3879, b3880, b3881, b3882, b3883, b3884 |
| GP35: | b1289, b1290, b1291, b1292, b1293, b1294, b1295, b1296, b1297, b1298, b1299, b1300, b1301, b1302 |
| GP36: | b2754, b2755, b2756, b2757, b2758, b2759, b2760, b2761 |
| GP37: | b0135, b0136, b0137, b0138, b0139, b0140, b0141 |
| GP38: | b0644, b0645, b0646, b0647, b0648, b0649, b0650 |
| GP39: | b0938,, b0939, b0940, b0941, b0942, b0943, b0944, b0945 |
| GP40: | b2219, b2220, b2221, b2222, b2223, b2224, b2225, b2226, b2227, b2228, b2229, b2230 |
| gp41: | b3376, b3377, b3378, b3379, b3380, b3381, b3382, b3383 |
| gp42: | b4084, b4085, b4086, b4087, b4088, b4089, b4090 |
| gp43: | b0530, b0531, b0532, b0533, b0534, b0535 |
| gp44: | b0730, b0731, b0732 |
| gp45: | b1483, b1484, b1485, b1486, b1487 |
| gp46: | b2270, b2271, b2272, b2273, b2274, b2275 |
| gp47: | b2332, b2333, b2334, b2335, b2336, b2337, b2338 |
| gp48: | b4321, b4322, b4323, b4324 |
| gp50: | b0716, b0717, b0718, b0719 |
| gp51: | b1653, b1654, b1655 |
| gp52: | b2735, b2736, b2737, b2738, b2739, b2740 |
| gp53: | b4265, b4266, b4267, b4268, b4269 |
| gp54: | b2405, b2406, b2407, b2408, b2409 |
| gp55: | b3897, b3898, b3899, b3900, b3901 |
| gp56: | b1201 |
| gp57: | b1580, b1581 |
| gp58: | b2108, b2109, b2110, b2111, b2112 |
| gp59: | b2364, b2365 |
| gp60: | b3213, b3214 |
| gp61: | b3686, b3687, b3688, b3689, b3690 |

TABLE 10

Completed Deletions from Parent Strain BL21(DE3)

| Deletion | Endpoints | Size (bp) | strain | notes |
|---|---|---|---|---|
| BMD1 | 15385-24623 | 9238 |  | equivalent to MD13 |
| BMD2 | 241256-243669 | 2413 |  | no MDS equivalent |
| BMD3 | 262791-264601 | 1810 | BL1 | no MDS equivalent |
| BMD4 | 352423-357555 | 5132 |  | approximately equivalent to MD16 |
| BMD5 | 376748-377531 | 783 |  | no MDS equivalent |
| BMD6 | 536916-592056 | 55140 | BL7 | approximately equivalent to MD12, MD61 and MD14 (DLP12 prophage+) |
| BMD7 | 619107-638679 | 19572 |  | includes MD57 |
| BMD8 | 658152-671312 | 13160 |  | includes MD47 |
| BMD9 | 1193606-1194384 | 778 |  | Precise deletion restore nagK and removes IS1 |
| BMD10 | 1322339-1325012 | 2673 |  | no MDS equivalent |
| BMD11 | 1398349-1451586 | 53237 |  | equivalent to MD2 includes rac prophage |
| BMD12 | 1460130-1460927 | 797 |  | Precise deletion restores cybB and removes IS1 |
| BMD13 | 1857061-1858411 | 1350 |  | Precise deletion restores yeaR and removes IS186 |
| BMD14 | 1973270-1974687 | 1417 | BL4 | No MDS equivalent |
| BMD15 | 2004159-2011036 | 6877 | BL2 | includes MD5 CP4-44 prophage |
| BMD16 | 2031433-2072701 | 41268 |  | includes MD22 colanic acid cluster |
| BMD17 | 2128600-2129378 | 778 |  | Precise deletion restores gatZ removes IS1 |
| BMD18 | 2139556-2143995 | 4439 | BL3 | No MDS equivalent |
| BMD19 | 2262740-2263509 | 769 |  | No MDS equivalent |
| BMD20 | 2406676-2408561 | 1885 |  | No MDS equivalent |
| BMD21 | 2616656-2618847 | 2191 |  | No MDS equivalent |
| BMD22 | 2677319-2685932 | 8613 |  | approximately equivalent to MD4, includes CP4-57 prophage |
| BMD23 | 2772836-2775877 | 3041 |  | No MDS equivalent |
| BMD24 | 2821970-2834720 | 12750 |  | No MDS equivalent - remove fuc operon |
| BMD25 | 2996251-3070465 | 74214 | BL5 | Similar to MD10 includes CP4-44 prophage |
| BMD26 | 3433461-3434239 | 778 |  | Precise deletion restores yhfS |
| BMD27 | 3651091-3662535 | 1444 |  | equivalent to MD39 |
| BMD28 | 3736504-3742367 | 5863 |  | removes IS1 in rfa gene cluster |
| BMD29 | 3893549-3894996 | 1447 | BL6 | no MDS equivalent |
| BMD30 | 4479765-4586245 | 106480 |  | approximately equivalent to MD9 and MD29 includes KplE2 prophage element |

TABLE 11

| Strain | lsequence | rsequence | Strain | lsequence | rsequence |
|---|---|---|---|---|---|
| BMD1 | Gaaaagtggcggggatcact (SEQ ID NO: 2) | Tacctcaatgtgtatcacaa (SEQ ID NO: 3) | BMD16 | Cattttatatgaaattactgaa (SEQ ID NO: 32) | Gtcattttacccgatagccg (SEQ ID NO: 33) |
| BMD2 | Gccatttttaatatagattg (SEQ ID NO: 4) | Gttctgctgatttaaccgca (SEQ ID NO: 5) | BMD17 | Tcaacatcatcgtttcgacg (SEQ ID NO: 34) | Ctatttttaatccgactatg (SEQ ID NO: 35) |
| BMD3 | Ggtcatgccaaccgcgacaa (SEQ ID NO: 6) | Ctgatttttaattaacgcgcg (SEQ ID NO: 7) | BMD18 | Gcagaagggcaccccgagtc (SEQ ID NO: 36) | Tgaacgttatccctgtagta (SEQ ID NO: 37) |
| BMD4 | Atagcgggcggcagaaggaa (SEQ ID NO: 8) | Tacgagagtggacggtcccc (SEQ ID NO: 9) | BMD19 | Gagaaatagtgcaggccgtc (SEQ ID NO: 38) | Gtccggcagataaagactaa (SEQ ID NO: 39) |
| BMD5 | Tccggcattaaaggaaaat (SEQ ID NO: 10)C | Ttaacgttgtgcttcgcca (SEQ ID NO: 11) | BMD20 | Aatcaacatggaataaaatc (SEQ ID NO: 40) | Tagtcagtgacgaacatcag (SEQ ID NO: 41) |
| BMD6 | Atcctgcagggcgcgccatt (SEQ ID NO: 12) | Ggagtaatccccgcatatcc (SEQ ID NO: 13) | BMD21 | Aagcgcggggagagttgcgt (SEQ ID NO: 42) | Tccgtcgaggattgcgcttt (SEQ ID NO: 43) |
| BMD7 | Acgcagattttttgcccat (SEQ ID NO: 14) | Atatgcccaataaattgtcg (SEQ ID NO: 15) | BMD22 | Caagctctgcgggcttttt (SEQ ID NO: 44) | Cctttgaaaacaggacgtaa (SEQ ID NO: 45) |
| BMD8 | Ccccggcccttgtttttatc (SEQ ID NO: 16) | Atatgcccaataaattgtcg (SEQ ID NO: 17) | BMD23 | Cgctggcgcggggaacaccc (SEQ ID NO: 46) | Caggttgatagaaatatcgc (SEQ ID NO: 47) |
| BMD9 | Gttggcggcgggctgatttt (SEQ ID NO: 18) | caacggcaaaccgattaccg (SEQ ID NO: 19) | BMD24 | Ctccttgttgctttacgaaa (SEQ ID NO: 48) | Cggaaagggtagcaggccgg (SEQ ID NO: 49) |
| BMD10 | Cgttccatggatggaagact (SEQ ID NO: 20) | Ttaagctgatgttaatcgaa (SEQ ID NO: 21) | BMD25 | Ttgcgggtatacctcagttc (SEQ ID NO: 50) | Agattacgccatttttgaatt (SEQ ID NO: 51) |
| BMD11 | Gcaacatcagcagccatacc (SEQ ID NO: 22) | Ttatgcagcaacaatgctgt (SEQ ID NO: 23) | BMD26 | Gcgcgcaacgttgccagcac (SEQ ID NO: 52) | Atctgccagcacgtagctgt (SEQ ID NO: 53) |
| BMD12 | Tcacagtgaaacgtaacgta (SEQ ID NO: 24) | Tactgaaaacgggtgaacaa (SEQ ID NO: 25) | BMD27 | Gtgttgatttccaacgagta (SEQ ID NO: 54) | Aactttgatttatagtcagg (SEQ ID NO: 55) |
| BMD13 | Ataacggaaaggcgtgggta (SEQ ID NO: 26) | Aaccccgggcgcgttcctt (SEQ ID NO: 27) | BMD28 | Aaaacgctgctatgatttaa (SEQ ID NO: 56) | Aaaattcttatcgataccgt (SEQ ID NO: 57) |
| BMD14 | Acgatgcctcaccgacgact (SEQ ID NO: 28) | Tccctgttacgttttaatgt (SEQ ID NO: 29) | BMD29 | Ctcaggtcgaaatctaacgc (SEQ ID NO: 58) | Cagacgcctcctttcttcat (SEQ ID NO: 59) |
| BMD15 | Tggtggcgactatgcactag (SEQ ID NO: 30) | Gcagaaactccgtaatgaag (SEQ ID NO: 31) | BMD30 | Tttttttatgcctgaaatcc (SEQ ID NO: 60) | Taaggcgagattattaaagt (SEQ ID NO: 61) |

REFERENCES

The following references, to the extent that they provide exemplary procedural or other details supplementary to those set forth herein, are specifically incorporated herein by reference:

U.S. Pat. No. 5,578,464
U.S. Pat. No. 5,747,662
U.S. Pat. No. 6,022,952
U.S. Pat. No. 6,335,178
U.S. Pat. No. 6,372,476
U.S. Pat. No. 6,472,16
Blattner et al., *Science*, 277:1453-1474, 1997.
*Current Protocols in Molec. Biol.*, 16.6.1-16.6.14, 1994.
Danese et al., *Annu. Rev. Genet.*, 32:59-94, 1998.
Datsenko et al., *Proc. Natl. Acad. Sci. USA*, 97:6640-6649, 2000.
Fekes et al., *Microbiol. Mol. Biol. Rev.*, 63:161-193, 1999.
Hanahan, *J. Mol. Biol.*, 166(4):557-580, 1983.
Hannig et al., *Trends Biotechnol.*, 16(2):54-60, 1998.
Hayashi et al., *DNA Res.*, 8:11-22, 2001.
Hockney, *Trends Biotechnol.*, 12(11): 456-632, 1994.
Hynds et al., *J. Biol. Chem.*, 273:34868-34874, 1998.
Muyrers et al., *Nucl. Acids Res.*, 27:1555-1557, 1999.
Neidhardt et al., *J. Bacteriol.*, 119(3):736-747, 1974.
Perna et al, *Nature*, 409:529-533, 2001.
Posfai et al., *J. Bacteriol.*, 179:4426-4428, 1997.
Posfai et al., *Nucl. Acids Res.*, 27:4409-4415, 1999.
Pugsley, *Microbiol. Rev.*, 57:50-108, 1993.
Sambrook et al., In: *Molecular Cloning. A Laboratory Manual*, Cold Spring Harbor Laboratory Press, Cold Spring Harbor, N.Y., 1989.
Santini et al., *EMBO J.*, 17:101-112, 1998.
Sargent et al., *EMBO J.*, 17(13):3640-3650, 1998.
Thomas et al., *Mol-Micro.*, 39(1):47-53, 2001.
Venkatesan et al., *Infection Immunity*, 3271-3285, 2001.
Weiner et al., *Cell*, 93:93-101, 1998.
Welch et al., *Proc. Natl. Acad. Sci. USA*, 99:26:17020-17024, 2002.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08765408B2). An electronic copy of the "Sequence Listing" will also be available from the USPTO upon request and payment of the fee set forth in 37 CFR 1.19(b)(3).

We claim:

1. A non-naturally occurring *Escherichia coli* (*E. coli*) bacterium having a genome between 4.41 Mb and 2.78 Mb and lacking CP4-6, DLP12, λ*B, RybB*B, e14, Rac, Qin, CP4-44, PR-X, KpLE1, CPZ-55, CP4-57, PheV*B, SelC*B, and KpLE2 prophage elements.

2. The bacterium of claim 1, wherein the bacterium additionally lacks all IS1, IS2, IS3, IS5, IS150 and IS186 insertion sequences.

3. The bacterium of claim 1, wherein the parent strain of said bacterium is a K12 or B strain.

4. The bacterium of claim 3, wherein the parent strain of said bacterium is K12 strain MG1655.

5. The bacterium of claim 3, wherein the parent strain of said bacterium is B strain BL21(DE3).

6. The bacterium of claim 1, wherein the bacterium comprises a vector.

7. The bacterium of claim 6, wherein the vector comprises a nucleic acid encoding a polypeptide and wherein the nucleic acid is operatively linked to an expression control sequence.

8. The bacterium of claim 7, wherein the vector is a plasmid.

9. A method of producing a polypeptide comprising culturing a bacterium according to claim 7 under suitable conditions to allow expression of the polypeptide and collecting the polypeptide.

10. The bacterium of claim 4, wherein the genome of the bacterium is lacking at least the nucleic sequences set forth in Table 1.

11. The bacterium of claim 1, wherein the chromosome of the bacterium does not comprise scars.

* * * * *